US008885177B2

(12) United States Patent
Ben-Yishai et al.

(10) Patent No.: US 8,885,177 B2
(45) Date of Patent: Nov. 11, 2014

(54) MEDICAL WIDE FIELD OF VIEW OPTICAL TRACKING SYSTEM

(71) Applicant: Elbit Systems Ltd., Haifa (IL)

(72) Inventors: Rani Ben-Yishai, Tel Aviv (IL); Adi Charny, Hod Hasharon (IL); Dror Yahav, Kfar Saba (IL); Shahaf Zommer, Ramat Yishai (IL); Ilan Efrat, Haifa (IL)

(73) Assignee: Elbit Systems Ltd., Haifa (IL)

( * ) Notice: Subject to any disclaimer, the term of this patent is extended or adjusted under 35 U.S.C. 154(b) by 0 days.

(21) Appl. No.: 14/085,960

(22) Filed: Nov. 21, 2013

(65) Prior Publication Data
US 2014/0078517 A1 Mar. 20, 2014

Related U.S. Application Data

(63) Continuation-in-part of application No. 13/746,587, filed on Jan. 22, 2013, now Pat. No. 8,593,647, which
(Continued)

(51) Int. Cl.
*G01B 11/14* (2006.01)
*G01S 3/784* (2006.01)
(Continued)

(52) U.S. Cl.
CPC .............. *G01B 11/002* (2013.01); *G01S 3/784* (2013.01); *A61B 5/066* (2013.01); *G01S 5/163* (2013.01); *A61B 5/055* (2013.01); *A61B 8/4254* (2013.01); *A61B 5/065* (2013.01); *A61B 6/12* (2013.01); *A61B 6/547* (2013.01)
USPC .......................................... 356/614; 356/623

(58) Field of Classification Search
CPC .... A61B 19/5244; A61B 19/52; A61B 19/54; A61B 2017/00725; A61B 2019/5265; A61B 2019/5483; A61B 19/20; A61B 19/46; A61B 19/5223; A61B 2019/262; A61B 2019/461; A61B 2019/467; A61B 2019/507
See application file for complete search history.

(56) References Cited

U.S. PATENT DOCUMENTS 3,678,283 A 7/1972 LaBaw
3,867,629 A 2/1975 Van Buskirk
(Continued)

FOREIGN PATENT DOCUMENTS

WO 9746893 12/1997
WO 2006061819 6/2006

OTHER PUBLICATIONS

International Search Report for PCT/IL2008/001252, dated Mar. 5, 2009, 4 pages.
(Continued)

*Primary Examiner* — Michael P Stafira
(74) *Attorney, Agent, or Firm* — Brown Rudnick LLP

(57) ABSTRACT

A medical Wide-Field-Of-View optical-tracking-system for determining the position and orientation of a target-object in a reference coordinate system. The system includes at least three light-emitters, at least one optical-detector and a processor. The processor is coupled with each optical-detector. One optical-detector is a Wide-Field-Of-View optical detector, which acquires an image of the light-emitters within the field-of-view thereof. Each Wide-Field-Of-View optical-detector includes an optical-sensor and two optical-receptors. The processor determines the position and orientation of the target-object in the reference coordinate system according to representations of the light-emitters. Each light-emitter is within the field-of-view of an optical-detector. Each optical-detector and each light-emitter is attached to one of the target-object and a reference-location. The target-object and the reference-location are respective elements in a tuple including two elements from a group consisting of a display, a patient-body-location, a-medical-tool, physician-body-location, and a fixed-position.

25 Claims, 16 Drawing Sheets

Related U.S. Application Data is a continuation of application No. 12/680,514, filed as application No. PCT/IL2008/001252 on Sep. 18, 2008, now Pat. No. 8,384,912.

(60) Provisional application No. 60/975,325, filed on Sep. 26, 2007.

(51) Int. Cl.
| | |
|---|---|
| *G01S 5/16* | (2006.01) |
| *A61B 8/00* | (2006.01) |
| *G01B 11/00* | (2006.01) |
| *A61B 5/06* | (2006.01) |
| *A61B 5/055* | (2006.01) |
| *A61B 6/12* | (2006.01) |
| *A61B 6/00* | (2006.01) |

(56) References Cited

U.S. PATENT DOCUMENTS

| | | | |
|---|---|---|---|
| 4,314,761 A | 2/1982 | Reymond et al. | |
| 4,576,481 A | 3/1986 | Hansen | |
| 4,585,948 A | 4/1986 | Schneider et al. | |
| 4,649,504 A | 3/1987 | Krouglicof et al. | |
| 4,684,247 A | 8/1987 | Hammill, III | |
| 4,684,249 A | 8/1987 | Ellis | |
| 5,196,689 A | 3/1993 | Sugita et al. | |
| 5,920,394 A | 7/1999 | Gelbart et al. | |
| 6,675,040 B1 * | 1/2004 | Cosman | 600/427 |
| 6,697,147 B2 | 2/2004 | Ko et al. | |
| 7,345,743 B1 | 3/2008 | Hartman et al. | |
| 7,623,224 B2 | 11/2009 | Vogel | |
| 8,295,909 B2 * | 10/2012 | Goldbach | 600/424 |
| 8,384,912 B2 | 2/2013 | Charny et al. | |
| 2003/0225329 A1 * | 12/2003 | Rossner et al. | 600/424 |
| 2004/0061041 A1 | 4/2004 | Ben-Ari et al. | |
| 2004/0138556 A1 * | 7/2004 | Cosman | 600/424 |
| 2008/0103509 A1 * | 5/2008 | Goldbach | 606/130 |
| 2014/0028548 A1 * | 1/2014 | Bychkov et al. | 345/156 |

OTHER PUBLICATIONS

International Preliminary Report on Patentability issued for PCT/IL2008/001252, dated Mar. 30, 2010, 8 pages.

Chang Kian Tan, "High Resolution Wide Angle Optical Position Detector," The University of British Columbia, Apr. 21, 1994, 86 pages.

Livingston, Mark A., "Vision-based Tracking with Dynamic Structured Light for Video See-through Augmented Reality," 1998, A Dissertation submitted to the faculty of The University of North Carolina at Chapel Hill, 145 pages.

C. C. H. Ma, et al., "Multi-Pinhole Wide-Angle High-Resolution Light Position Detector," IEEE Transactions on Instrumentation and Measurement, vol. 45, No. 1, Feb. 1996, pp. 195-200.

Trein, J., et al., "FPGA Implementation of a Single Pass Real-Time Blob Analysis Using Run Length Encoding," MPC-Workshop Feb. 2008, 7 pages.

Welch, G., et al., "High-Performance Wide-Area Optical Tracking," The HiBall Tracking System, Presence, vol. 10, No. 1, Feb. 2001, pp. 1-21.

Vallino, J. R., "Augmenting Reality with Minimal Calibration," Thesis Proposal, Department of Computer Science, University of Rochester, Jun. 17, 1998, 44 pages.

M.Sc. Yuning Yang, "Design and Implementation of a Scalable Hardware Platform for High Speed Optical Tracking," Inaugural—Dissertation, Oct. 30, 2012, 190 pages.

* cited by examiner

'MEDICAL WIDE FIELD OF VIEW OPTICAL TRACKING SYSTEM

CROSS REFERENCE

This application is a continuation in part of U.S. patent application Ser. No. 13/746,587 which is a continuation of U.S. patent application Ser. No. 12/680,514 (now U.S. Pat. No. 8,384,912), filed as a national phase of PCT Application PCT/IL2008/001252, which claims priority from U.S. Provisional Patent Application 60/975,325 filed on Sep. 26, 2007. Each of these four other applications is incorporated herein in its entirety.

FIELD OF THE DISCLOSED TECHNIQUE

The disclosed technique relates to tracking systems, in general, and to a Wide Field Of View (WFOV) optical tracking system for determining the position and orientation of a moving object, in particular.

BACKGROUND OF THE DISCLOSED TECHNIQUE

Optical tracking systems for tracking the position and orientation of a moving object in a reference coordinate system are known in the art. These tracking devices employ optical detectors (e.g., Charge Coupled Devices) for gathering information about the position and/or orientation of a moving object. One configuration for such an optical tracking device is fixing one or several optical detectors on the moving object and fixing a set of light sources (e.g., Light Emitting Diodes) at a known position in the coordinate system. Another configuration for such an optical tracking device is fixing a set of light sources on the moving object and fixing one or several optical detectors at a known position in the reference coordinate system. Yet another configuration is combining the former configurations and fixing both detectors and light emitters on the moving object and at a known position in the reference coordinate system. Optical tracking systems enable automatic decision making based of the determined position and/or orientation. For example, a pilot may aim at a target by moving only her head toward the target (i.e., the pilot does not have to move the aircraft toward the target). The optical tracking system determines the orientation (i.e., elevation, azimuth and roll) of the helmet, worn by the pilot, in the aircraft coordinate system. As a further example, the optical tracking system may track the movements of a user of a virtual reality system (e.g., a game, a simulator) determining the position of the user.

However, an optical detector placed on the moving object can detect the light emitters in the reference coordinate system only as long as the light emitters are within the Field Of View (FOV) of the detector. Therefore, the FOV of the optical tracking system (i.e., the range of positions in which the optical tracking system tracks the moving object) is limited by the FOV of the optical detector. Similarly, the fixed light detector can track the moving object as long as the light emitters attached to the moving object are within the FOV of the fixed light detector. Thus, the intersection of the FOV of the moving light detector, with the FOV of the fixed light detector, defines the tracking space of the tracking system.

Reference is now made to FIG. 1, which is a schematic illustration of an optical detector, generally referenced 10, which is known in the art. Optical detector 10 includes an optical sensor 12 optically coupled with a lens 14. Lens 14 includes an entrance pupil 16. The FOV $\phi$ of optical detector 10 is inversely proportional to the ratio between the focal length f of lens 14 and the size d of optical sensor 12. Furthermore, the accuracy of optical detector 10 is proportional to the angular resolution thereof. Therefore, when the size of sensor 12 (e.g., number of pixels) is fixed, increasing the focal length of lens 14, increases the resolution but decreases the FOV of optical detector 10.

U.S. Pat. No. 3,678,283 issued to LaBaw, and entitled "Radiation Sensitive Optical Tracker", is directed to a system for determining the sight line of a pilot with respect to a point in a cockpit. The optical tracker includes: two detector assemblies and three light emitters. The first detector assembly is mounted on the helmet of the pilot. The first light emitter is mounted on the helmet of the pilot. The second detector assembly is mounted on the cockpit, at the point. The second and third light emitters are mounted on the cockpit, equally spaced on either side of the bore sight line in front of the pilot.

The detector assemblies include lateral photo detectors able to detect the lateral position of the light spot. The light emitters illuminate at a light frequency corresponding to the maximum sensitivity range of the detectors. The two light emitters mounted on the cockpit illuminate the detector mounted on the helmet. The illuminator mounted on the helmet illuminates the detector mounted on the cockpit. The determination of the azimuth and elevation angles, of the line of sight of the pilot, is irrespective of the helmet position within the cockpit. The amount of roll of the head of the pilot is computed by the output of the helmet mounted detector, which detects the two cockpit mounted light emitters.

U.S. Pat. No. 5,767,524 issued to Barbier et al., and entitled "Optical Device for Determining the Orientation of a Solid Body", is directed to a system for determining the orientation of a first solid body with respect to a second solid body. The orientation determination system includes: three sets of optical source/detector. Each optical source/detector set includes an optical source and an optical radiation detector. At least one source/detector set is mounted on the first solid body. At least one source/detector set is mounted on the second solid body. On at least one of the solid bodies there are mounted two source/detector sets.

The orientation system determines in the first referential system, of the first solid body, two straight lines corresponding to the light radiation coming from the second referential system. The orientation system determines in the second referential system, of the second solid body, two straight lines corresponding to the light radiation coming from the first referential system. The knowledge of the orientation of at least two distinct straight lines in each of the referential systems gives, by computation of the rotation matrix, the three parameters of orientation of the first solid body with respect to the referential system of the second solid body.

SUMMARY OF THE PRESENT DISCLOSED TECHNIQUE

It is an object of the disclosed technique to provide a novel system determining the position and orientation of a moving object in a reference coordinate system.

In accordance with one aspect of the disclosed technique, there is thus provided a medical Wide Field Of View optical tracking system for determining the position and orientation of a target object in a reference coordinate system. The system includes at least three light emitters, at least one optical detector and a processor. The processor is coupled with each of the at least one optical detector. At least one of the at least one optical detector is a Wide Field Of View optical detector, which acquires at least one image of at least one light emitter within the field of view thereof. Each Wide Field Of View optical detector includes an optical sensor and two optical receptors. The optical sensor senses light received from the at least one light emitter within the field of view of the Wide Field Of View optical detector. The optical receptors are optically coupled with the optical sensor. Each optical receptor includes an entrance pupil. The optical receptors are spatially spaced apart from each other and each projects a different angular section of an observed scene on the optical sensor. The processor determines the position and orientation of the target object in the reference coordinate system, at least according to representations of the at least three light emitters. Each of the at least three light emitters is within the field of view of at least one of the at least one optical detector. Each one of the at least one optical detector and each one of the at least three light emitters is adapted to be attached to a respective one of the target object and a reference location. The reference location is associated with a reference coordinate system. The target object and the reference location are respective elements in a tuple including two elements from a group consisting of a display, a patient body location, a medical tool, physician body location, and a fixed position.

In accordance with another aspect of the disclosed technique, there is thus provided a medical WFOV optical tracking system for determining the position and orientation of a target object in a reference coordinate. The system includes at least one light emitter attached to the target object, at least two light emitters attached to a head mounted display, a Wide Field Of View optical detector, an optical detector and a processor. The processor is coupled with the Wide Field of View optical detector, with the optical detector and with the head mounted display. The target object is of one of at least one of a patient and a medical tool. The head mounted display is located on the head of the physician and is associated with a reference coordinate system. The Wide Field Of View optical detector is attached to the target object and acquires at least one image of each at least two light emitters attached to the head mounted display within the field of view thereof. The Wide Field Of View optical detector includes an optical sensor, for sensing light received from at least one of the at least two light emitters attached to the head mounted display. Each of the optical receptors includes an entrance pupil. The optical receptors are spatially spaced apart from each other. Each of the optical receptors projects a different angular section of an observed scene on the optical sensor. The optical detector is attached to the head mounted display and acquires at least one image of each of the at least one light emitter attached to the target object within the field of view thereof. The processor determines the position and orientation of each of each target object in the reference coordinate system, according to representations of the at least one light emitter attached to the target object and the at least one other light emitter attached to the reference location. The head mounted display displays a least one rendered model of the patient and a representation the medical tool, to the physician, at an orientation corresponding to the determined orientation of the at least one selected target object.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing an optical tracking system for determining the pose of a moving object including a moving optical detector and a reference optical detector. The term "pose" relates hereinafter to the position (i.e., the x, y and z coordinates) and the orientation (i.e., azimuth elevation and roll angles). According to one embodiment of the disclosed technique, the moving optical detector exhibits a novel configuration, for increasing the FOV thereof, without increasing the size of the optical sensor or decreasing the focal length of the optical receptor (i.e., which decreases the accuracy of the tracking system). According to another embodiment of the disclosed technique, the spatial setup of the light emitters and the detectors enables the optical tracking system to determine the orientation of a moving object (e.g., a helmet, a stylus, a medical needle, an ultrasound imager), in a reference coordinate system (e.g., the coordinate system of an aircraft), without determining the position of the moving object. According to a further embodiment of the disclosed technique, a reflective surface replaces the reference detector, and also enables the optical tracking system to determine the orientation of a moving object, in a reference coordinate system, without determining the position of the object.

As mentioned above an optical detector, placed on a moving object, can detect light emitters that are situated within the FOV of that optical detector. Therefore, increasing the FOV of the optical detector increases the tracking range of the tracking system. In order to increase the FOV of the optical detector a plurality of optical receptors (e.g., lenses or pinholes or both) are placed over an optical sensor. Additionally, the optical axes of the optical receptors may be unparallel with respect to each other. Thus, the field of view of the detector is increased (i.e., relative to the FOV of a single optical receptor). Furthermore, the focal length of each optical receptor may be different. It is noted that the WFOV optical detector according to the disclosed technique, resolves objects in the WFOV thereof, when the angular span of these objects is substantially small (i.e., point like objects), such that the images of the object, formed on the optical sensor by the various lenses, do not overlap with each other.

Figure 1:
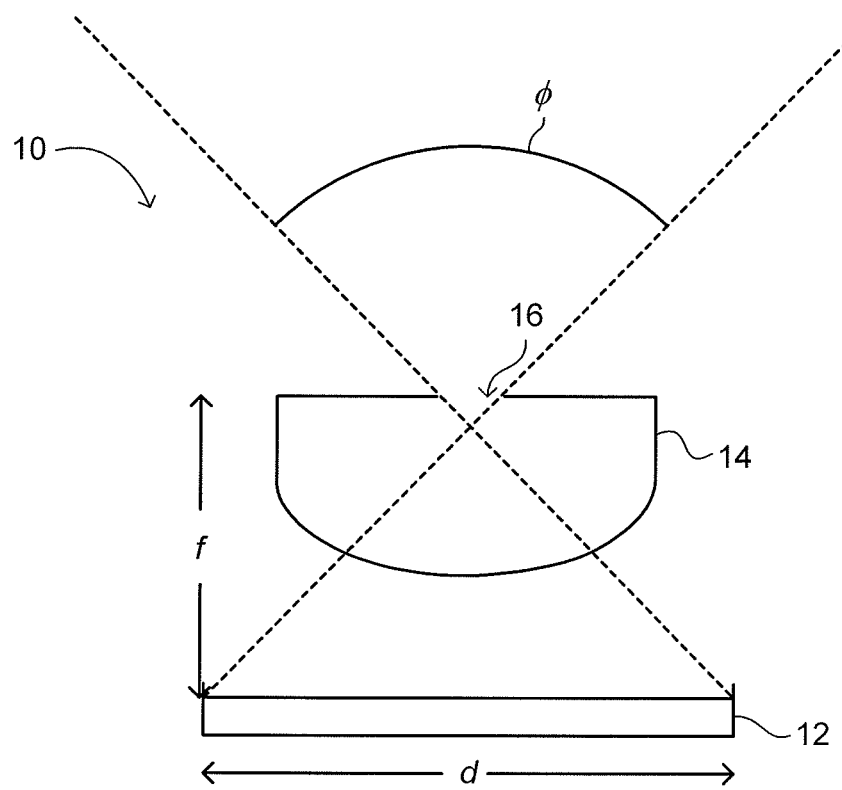
FIG. 1 is a schematic illustration of an optical detector, generally referenced 10, which is known in the art.
Figure 2A:
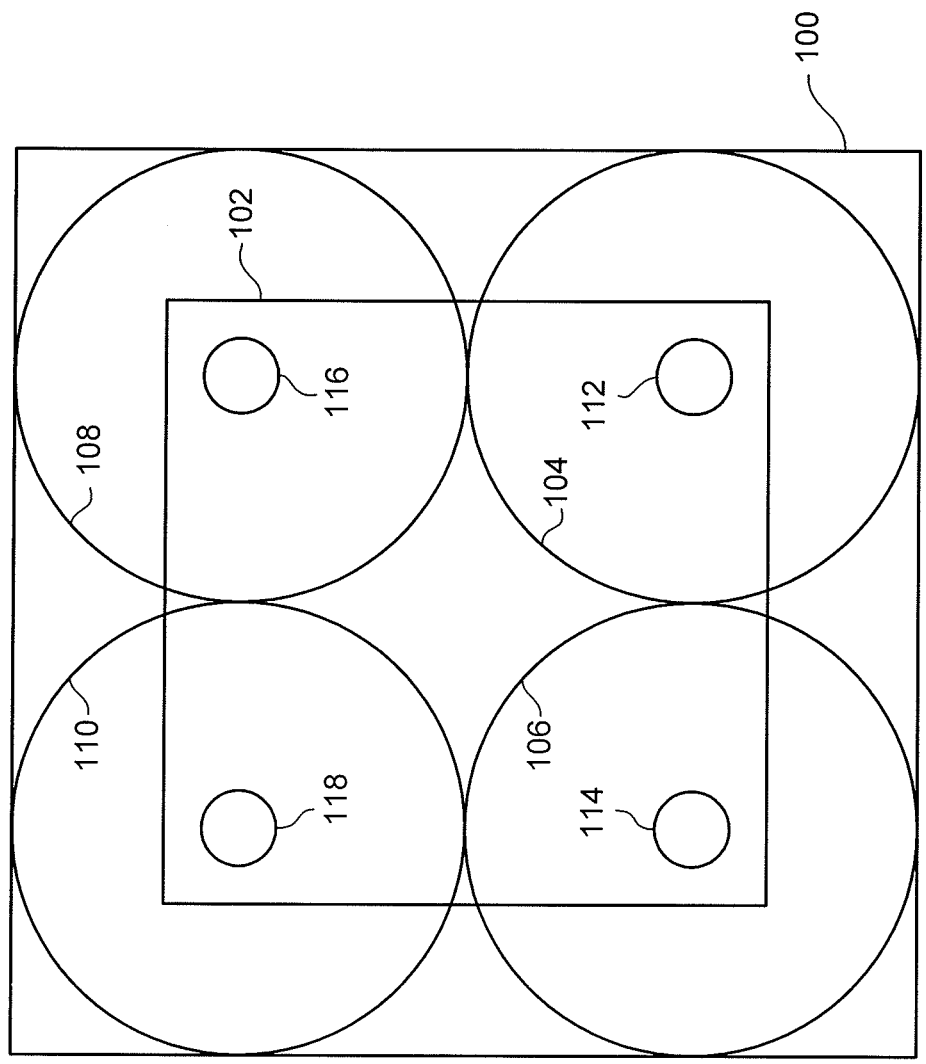
FIGS. 2A and 2B are schematic illustrations of a WFOV optical detector assembly, generally referenced 100, constructed and operative in accordance with an embodiment of the disclosed technique.
Figure 2B:
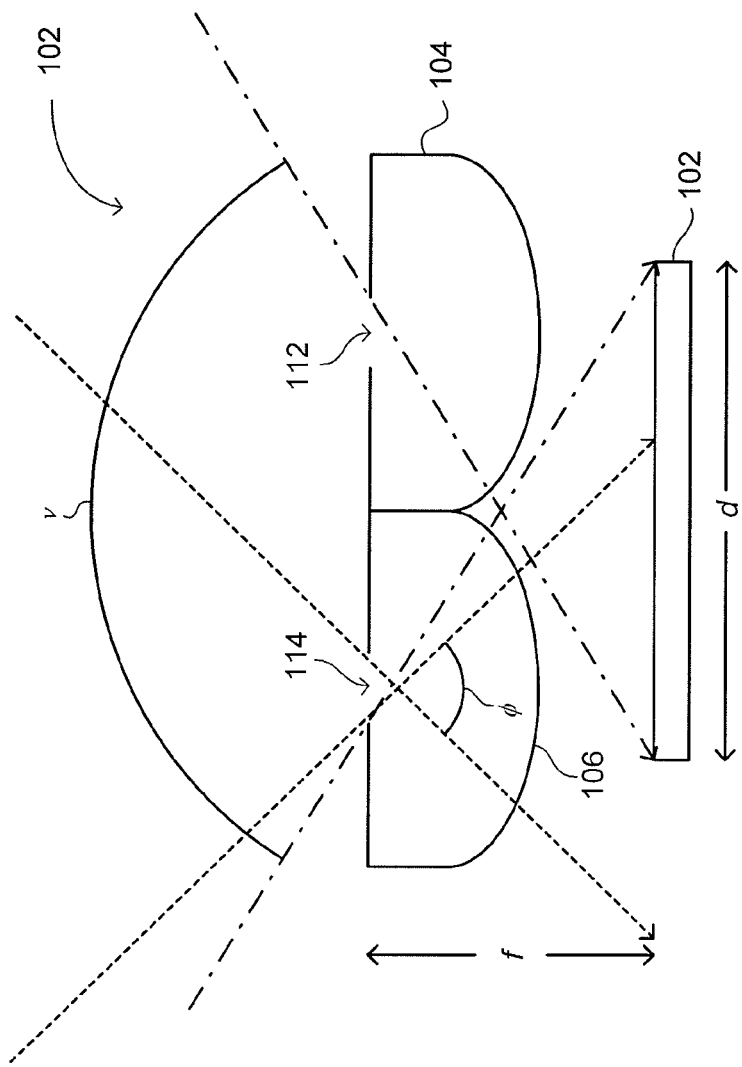

Reference is now made to FIGS. 2A and 2B, which are schematic illustrations of a WFOV optical detector assembly, generally referenced 100, constructed and operative in accordance with an embodiment of the disclosed technique. FIG. 2B is a side view of optical detector assembly 100. Optical detector assembly 100 includes an optical sensor 102 and optical receptors 104, 106, 108 and 110. Optical receptors 104, 106, 108 and 110 are spaced apart from each other. Each one of optical receptors 104, 106, 108 and 110 includes an entrance pupil. Optical receptor 104 includes an entrance pupil 112, optical receptor 106 includes an entrance pupil 114, optical receptor 108 includes an entrance pupil 116 and optical receptor 110 includes an entrance pupil 118. Optical receptors 104, 106, 108 and 110 may be optical lenses. Alternatively, Optical receptors 104, 106, 108 and 110 may be pinholes.

Optical receptors 104, 106, 108 and 110 are optically coupled with optical sensor 102. Optical sensor 102 is, for example, a CCD detector, a Complementary Metal Oxide Semiconductor (CMOS) sensor, a Position Sensitive Device (PSD) or a lateral photo-detector. Optical receptors 104, 106, 108 and 110 are arranged such that each element projects different angular sections of the observed scene (not shown) on the same area of optical sensor 102. The FOV $\nu$ (FIG. 2B), of optical detector assembly 100 is greater than FOV $\phi$ (FIG. 2B) of a single optical receptor such as optical receptor 106. Thus, the FOV of optical detector assembly 100 is increased (i.e., relative to the FOV of a single element) without increasing the size d (FIG. 2B) of optical detector 100 or decreasing the focal length f (FIG. 2B) of optical detector assembly 100.

To increase the resolution at the center of the FOV of the optical detector, an additional optical receptor, with a larger focal length, is placed above the optical receptors. Furthermore, to increase the FOV of the optical detector the bottom optical receptors are tilted, relative to one another, such that the optical axes thereof are unparallel.

Optical detector 100 exhibits a unique response to the direction of light incident thereupon. The position of the light incident on optical sensor 102 is related to the direction from which light enters each of entrance pupils 112, 114, 116 and 118. The unique response of the optical detector to the direction of light incident thereupon is referred to herein as the "directional response". For example, when the optical sensor 102 is a CCD sensor, each pixel in the CCD is associated with an angular step. When the optical sensor is a lateral photo-detector, the current differences at the terminals of the detector are related to the angle of light incident on the lateral photo-detector.

Figure 3A:
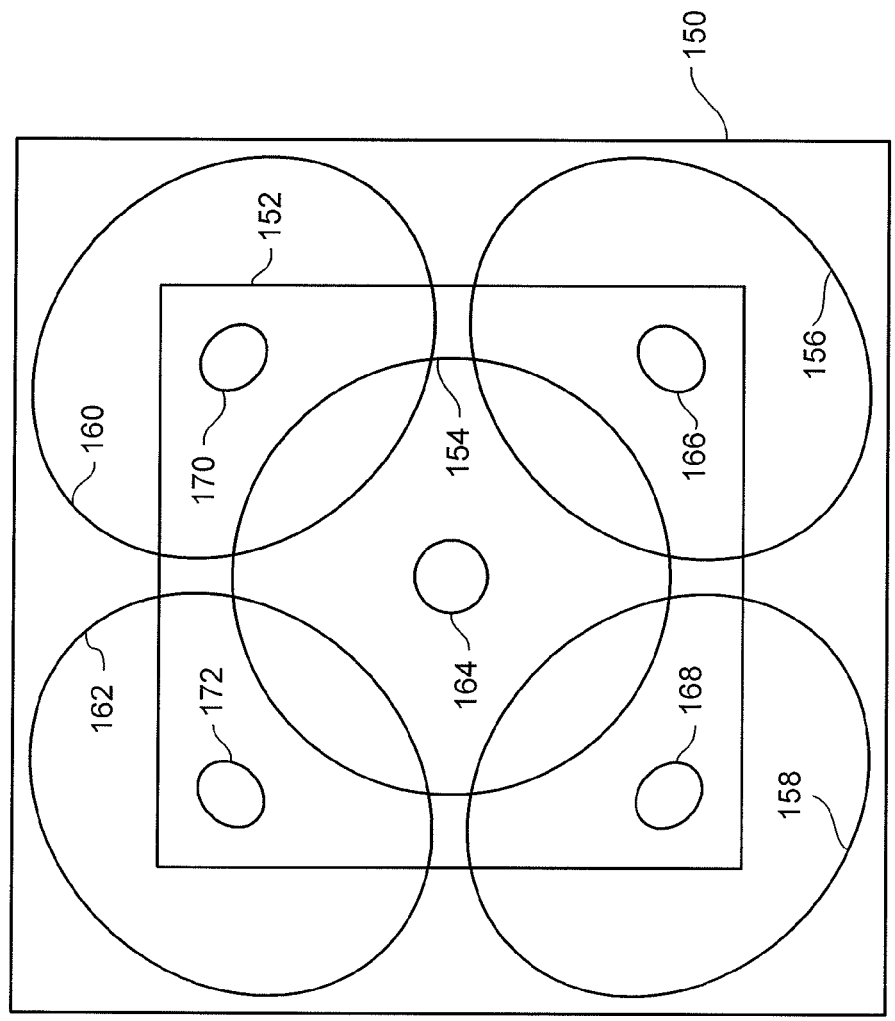
FIGS. 3A and 3B are schematic illustrations of WFOV optical detector assembly, generally referenced 150, constructed and operative in accordance with another embodiment of the disclosed technique.
Figure 3B:
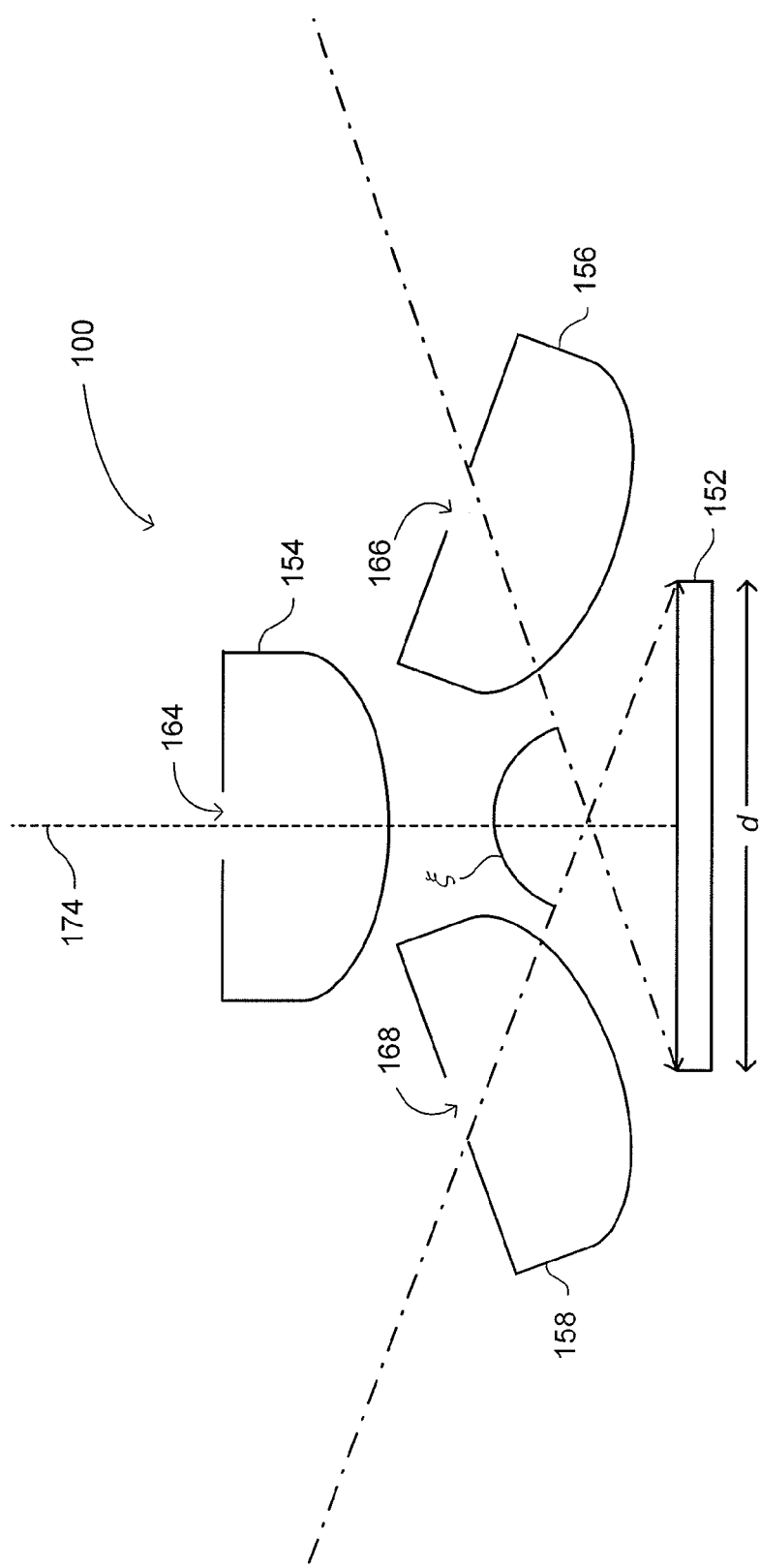

Reference is now made to FIGS. 3A and 3B, which are schematic illustrations of WFOV optical detector assembly, generally referenced 150, constructed and operative in accordance with another embodiment of the disclosed technique. FIG. 3B is a side view of optical detector assembly 150. Optical detector assembly 150 includes an optical sensor 152 and optical receptors 154, 156, 158, 160 and 162. Optical receptors 154, 156, 158, 160 and 162 are spaced apart from each other. Each one of optical receptors 154, 156, 158, 160 and 162 includes an entrance pupil and a lens. Optical receptor 154 includes an entrance pupil 164, optical receptor 156 includes an entrance pupil 166, optical receptor 158 includes an entrance pupil 168, optical receptor 160 includes an entrance pupil 170 and optical receptor 162 includes an entrance pupil 172.

Optical receptors 154, 156, 158, 160 and 162 are optically coupled with optical sensor 152. The FOV $\xi$ (FIG. 3B), of optical detector assembly 150 is increased relative to the FOV of a single optical receptor (e.g., optical receptor 106 in FIG. 2B) without changing the size d of optical sensor 152 or the focal lengths of the lenses. As mentioned above optical receptors 154, 156, 158,160 and 162 may be optical lenses. Alternatively, optical receptors 154, 156, 158, 160 and 162 may be replaced with pinholes. Optical detector 150 exhibits a directional response.

Figure 4:
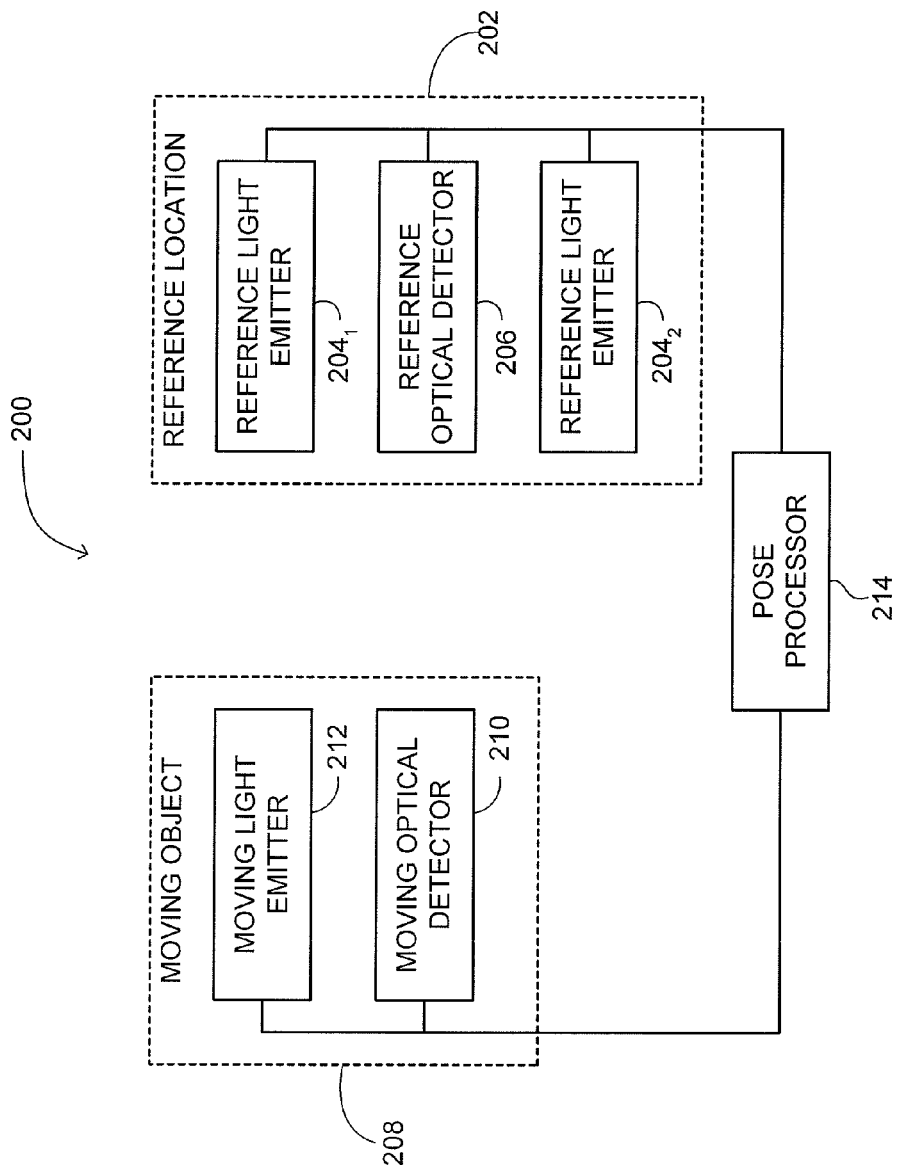
FIG. 4 is a schematic illustration of an optical tracking system, generally referenced 200, for determining the pose (i.e., position and orientation) of a moving object 208 in a reference coordinate system in accordance with a further embodiment of the disclosed technique.
Figure 5C:
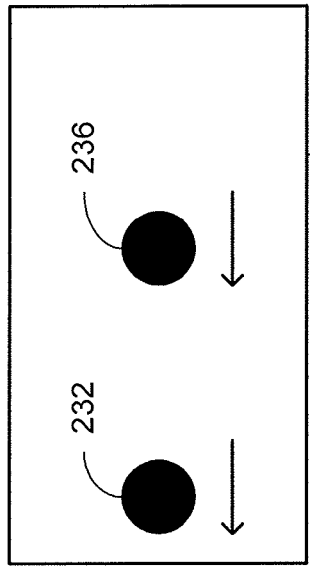
FIGS. 5A, 5B, 5C and 5D are schematic illustrations of images of a single light emitter acquired by a WFOV optical detector which includes only two adjacent optical receptors.
Figure 5D:
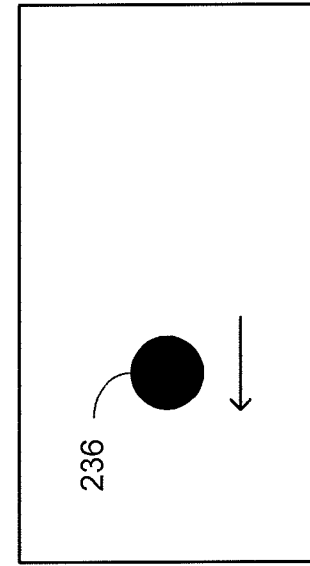
Figure 5A:
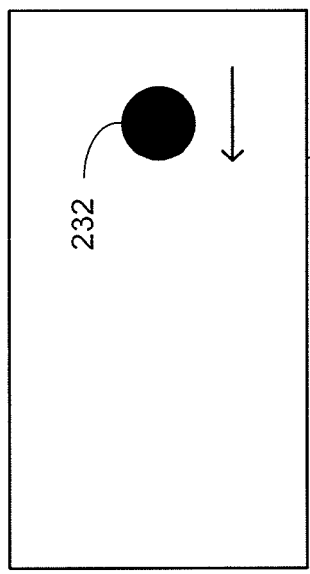
Figure 5B:
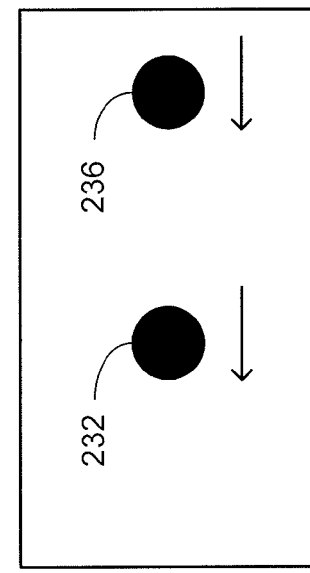

Reference is now made to FIG. 4, which is a schematic illustration of an optical tracking system, generally referenced 200, for determining the pose (i.e., position and orientation) of a moving object 208 in a reference coordinate system in accordance with a further embodiment of the disclosed technique. System 200 includes a reference optical detector 206, reference light emitters $204_1$ and $204_2$, moving optical detector 210, a moving light emitter 212 and a pose processor 214. Either one of reference optical detector 206 or moving optical detector 210 may be a WFOV optical detector as described hereinabove in conjunction with FIGS. 2A and 2B or FIGS. 3A and 3B. Pose processor 214 is coupled with reference optical detector 206 and with moving optical detector 210. When reference light emitters $204_1$ and $204_2$ and moving light emitter 212 are light sources (e.g., LEDs), pose processor 214 is optionally coupled therewith. Reference optical detector 206 and reference light emitters $204_1$ and $204_2$ are situated at a known position 202 in a reference coordinate system (not shown). In general, reference optical detector 206 and moving optical detector 210 may be wired or wirelessly coupled with pose processor 214 and transmit information relating to the image or images acquired thereby over a wireless communication channel and employing a wireless communication protocol (e.g., Bluetooth or WiFi).

Moving optical detector 210 and moving light emitter 212 are attached to moving object 208. Moving light emitter 212 and reference light emitters $204_1$ and $204_2$ are, for example, Light Emitting Diodes (LEDs) emitting light at a desired spectral range (e.g., visible light, infrared). Each of reference optical detector 206 and moving optical detector 210 exhibit a directional response. Each of reference optical detector 206 and moving optical detector 210 include an optical sensor (not shown). The optical sensors are, for example, Charge Coupled Devices (CCDs), Complementary Metal Oxide Semiconductor (CMOS) sensor, a Position Sensitive Device (PSD) or a lateral photo-detector.

Reference light emitters $204_1$ and $204_2$ and moving light emitter 212 emit light either periodically (i.e., light pulses) or continuously. Reference optical detector 206 acquires an image or images of moving light emitter 212. Moving optical detector 210 acquires an image or images of reference light emitters $204_1$ and $204_2$. The term "acquires an image" refers herein to the exposure of the sensor in the detector to light and the accumulation of energy in the sensor pixels. Reference optical detector 206 and moving optical detector 210 provide information relating to the acquired image or images to pose processor 214.

According to one alternative, the information relating to the acquired image relates to a pre-processed image or a pre-processed portion of the image. In other words, reference optical detector 206 and moving optical detector 210 sample the energy values of at least a portion of the sensor pixels, and pre-process the sampled pixels (i.e., pre-process at least a portion of the image). This pre-processing includes, for example, filtering, segmenting (e.g., Binary Large Object—BLOB detection), scaling, rotating and the like. Alternatively or additionally, reference optical detector 206 and moving optical detector 210 provide information relating to objects in the image (i.e., as determined during segmentation). This information relates, for example, to the size, location, color, texture of the object and the like.

According to another alternative, the information relating to the acquired image refers to the sampled energy values of at least a portion of the sensor pixels. In other words, reference optical detector 206 and moving optical detector 210 sample the energy values of at least a portion of the sensor pixels (i.e., at least a portion of the acquired image) and provide the sampled pixels to pose processor 214. Pose processor 214 pre-processes the sampled image (or the portion thereof).

When reference optical detector 206 and moving optical detector 210 acquire an image or images of light emitters 212, $204_1$ and $204_2$, the information relating to the acquired images include information relating to light emitters 212, $204_1$ and $204_2$. The information relating to light emitters 212, $204_1$ and $204_2$ is referred to herein as "representations" of the light emitters. These representations may be the sampled image or images or information relating to objects in the image associated with light emitters 212, $204_1$ and $204_2$. Pose processor 214 determines the pose of moving object 208 relative to the reference coordinate system according to the representations of light emitters 212, $204_1$ and $204_2$ provided thereto by reference optical detector 206 and moving optical detector 210.

In general to determine the position and orientation of moving object 208, pose processor 214 generates and solves at least six equations with six unknowns (e.g., three unknowns for position, the x, y and z coordinates and three unknowns for orientation, the azimuth elevation and roll angles). A representation of a light emitter is associated with two angles. For example, when the optical sensor is a CCD sensor, that CCD sensor is associated with a physical center. An imaginary line passing through this physical center, perpendicular to the sensor plane, defines the optical axis of the CCD sensor. Each pixel in CCD sensor is associated with a respective location on the CCD sensor, defined by a sensor 2D coordinates system in pixel units (e.g., a pixel located at coordinates [2:3] in the sensor 2D coordinates system is the pixel at the intersection of the second colon of pixels with the third row of pixels). Accordingly, each pixel is associated with a horizontal angle and a vertical angle from the optical axis of the sensor, related to the location of the pixel in the sensor 2D coordinate system. Consequently, each representation of a light emitter determined from an image acquired by the CCD sensor is also associated with a respective horizontal angle and a vertical angle from the center of the optical axis of the CCD sensor.

Thus, the representation of moving light emitter 212 determined from the image acquired by reference optical detector 206 is associated with two respective angles. Furthermore, each representation of each reference light emitter $204_1$ and $204_2$ determined from the image acquired by moving optical detector 210 is also associated with two respective angles. Accordingly a total of six measurements of angles are acquired, along with the known spatial relationship (i.e., relative position) between reference light emitters $204_1$ and $204_2$ and optical detector 206, and the known spatial relationship between moving light emitter 212 and optical detector 210, define the above mentioned six equations with six unknowns. Pose processor, 214 solves these equations to determine the position and orientation of moving object 208 in reference coordinate system. When a single optical detector is employed, which acquires an image of at least three light emitters, the two angles associated with each representation along with the known spatial relationship between the light emitters define the above mentioned six equations with six unknowns.

It is noted that system 200 can determine the pose of moving object 208 as long as reference light emitters $204_1$ and $204_2$ are within the FOV ν of moving optical detector 210 and as long as moving light emitter 212 is within the FOV of reference optical detector 206. It is further noted that when moving optical detector 210 is a WFOV optical detector, each optical receptor projects a respective representation of light emitters $204_1$ and $204_2$ on the optical sensor of moving optical detector 210.

Pose processor 214 associates the representations of light emitters $204_1$ and $204_2$ with the respective optical receptor, projecting these representations on the optical sensor. The first association of a representation and an optical receptor can be performed, for example, based on a low-accuracy tracking system such as an inertial tracker which provides a position and orientation. According to this example, the pose processor 214 determines a position and orientation of each possible association between a representation and an optical receptor and chooses the association in which the orientation is most similar to that determined by the low-accuracy tracker (e.g., an inertial tracker or a magnetic tracker). Alternatively, pose processor 214 associates the representations of light emitters $204_1$ and $204_2$ with the respective optical receptor, projecting these representations on the optical sensor, by determining a figure of merit for each representation. Pose processor 214 selects the association with the higher figure of merit. To that end, for each set of representations, processor 214 determines respective position and orientation of moving object 208. In the process of solving these equations (e.g., employing least squares), each solution, respective of each association between representations and a receptor, is associated with a respective residual error. Processor 214 selects the solution and thus the association with the smallest respective residual error (i.e., the figure of merit is the inverse, or an increasing function of the inverse of the residual error). In yet another alternative, when light emitters $204_1$ and $204_2$ are in the FOV of at least two of the optical receptors of moving optical detector 210, pose processor 214 associates the representations of light emitters $204_1$ and $204_2$ with the respective optical receptors according to the geometric configuration of the optical receptors. After associating each light emitter with a respective optical once, pose processor 214 tracks the representations of light emitters $204_1$ and $204_2$ on the optical sensor, and thus the association of the representations of light emitters with the respective optical receptor is maintained in the following cycles as further explained below.

When processing an image or images acquired by moving optical detector 210 and reference optical detector 206, it is not required to process the image in its entirety. Rather the pre-processing, performed either by pose processor 214 or by reference optical detector 206 and moving optical detector 210, is performed only over a predefined region of interest (ROI) within the image. The borders of the ROI are updated on a frame-by-frame basis. The ROI borders are determined according to the predicted locations of the representations of the light emitters in the acquired image, for example, based on the estimated relative orientation between the moving object and the reference location as determined by a low accuracy tracker. Alternatively, the ROI borders are determined according to the location of the representations of the light emitters in a previous image or images and an estimation of motion of moving optical detector 210. In general more than one ROI may be generated in order to track two or more groups emitters with minimal latency.

Although in FIG. 4, the optical detector 210 is described as a moving optical detector and optical detector 206 as a reference optical detector, it is noted that, in general, these two detectors may exhibit relative motion there between (i.e., either one or both of optical detector 206 and optical detector 210 may move). The coordinate system in which the object is tracked may be that associated with the reference optical detector. Thus, an optical tracking system such as optical tracking system 200 may be employed for various tracking applications. For example, a tracking system similar to optical tracking system 200 may be employed in medical navigation applications, such as described below. It is further noted that any one of the light emitters described herein above and below may be a light source or a light reflector (e.g., ball reflector) which reflects light incident thereon (i.e., either ambient light, light from various light sources located at the vicinity of the light reflector or from a dedicated light source directing light toward the light reflector).

Reference is now made to FIGS. 5A, 5B, 5C and 5D which are schematic illustrations of images of a single light emitter acquired by a WFOV optical detector which includes only two adjacent optical receptors (not shown). In FIGS. 5A, 5B, 5C and 5D the WFOV optical detector moves from left to right relative to the light emitter. Consequently, emitter representation 232 and 236 of the light emitter (not shown), in images 230, 234, 238 and 240, move from right to left (i.e., relative to the image vertical axis), as designated by the arrow. In image 230 (FIG. 5A), emitter representation 232 represents the light received from the light emitter and received by the first optical receptor. In images 234 and 238 (FIGS. 5B and 5C), emitter representations 232 and 236 represent the light received from the light emitter and received by both the optical receptors. In image 240 (FIG. 5D), emitter representation 236 represents the light received from the light emitter and received by the second optical receptor. Thus, by tracking the representations of the light emitter, a pose processor (e.g., pose processor 214 in FIG. 4) determines which optical receptor in the WFOV optical detector projects the light received from a light emitter. During initialization of the system or when the optical tracking system loses track of the moving object, the optical tracking system has no information relating to which one of the optical receptors projects light on the optical sensor. Therefore, the system determines the correct association using one of the above mentioned methods.

According to another embodiment of the disclosed technique, the spatial setup of the light emitters and the detectors enables the optical tracking system to determine the orientation of a moving object, in a reference coordinate system, without determining the position of the object. According to this spatial setup, a light emitter is placed at the entrance pupil of each optical receptor and emits light therefrom. Alternatively, a virtual representation of the light emitter can be created at the entrance pupil of the optical receptor (e.g., using beam splitters situated in front of the entrance pupil of the optical receptor). Consequently, the light emitter is perceived as emitting light from the entrance pupil of the optical receptor. In yet another alternative, two light emitters are placed such that the optical center of gravity thereof (e.g., the average position vector, in the reference coordinate system, of the two light emitters) is located at the entrance pupil of the optical receptor. Referring back to FIG. 4, a virtual representation (not shown) of light emitter 212 is formed at the entrance pupils of the optical receptors of moving optical detector 210. Reference light emitters $204_1$ and $204_2$ are positioned such that the optical center of gravity thereof is located at the entrance pupil of the optical receptor of reference optical detector 206. Consequently orientation processor determines the orientation of moving object 208 without determining the position thereof.

Figure 6:
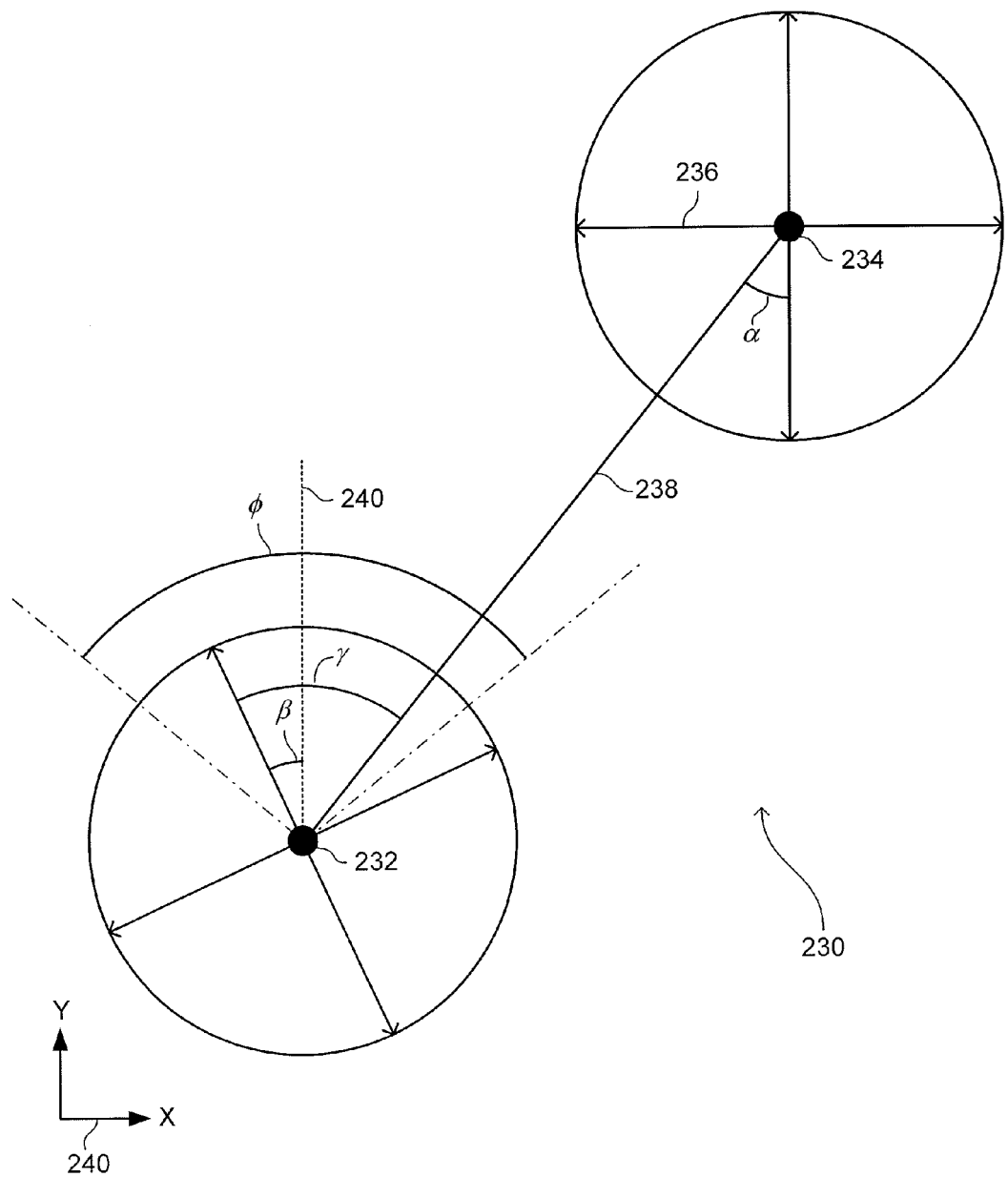
FIG. 6 is an example for determining the horizontal orientation of a moving object without determining the position thereof in accordance with another embodiment of the disclosed technique.

Reference is now made to FIG. 6 which is an example for determining the horizontal orientation of a moving object without determining the position thereof in accordance with another embodiment of the disclosed technique and still referring back to FIG. 4. It is noted that in exemplary FIG. 6, the position of moving object 208 changes in the X, Y plane of two-dimensional (2D) coordinate system 240, and the orientation of moving object 208 may change only horizontally. It is further noted that the example brought herein is operative in either one of two cases. In the first case the light emitters emit light from the entrance pupil of the optical receptor of the optical detector. In the second case at least two light emitters are situated such the optical center of gravity thereof is located at the pupil of the optical detector. It is also noted that the roll angle is assumed to be zero.

Pose processor 214 determines the angle α, between the longitudinal axis 240 of reference coordinate system 236 and line 238 connecting entrance pupil 232 and entrance pupil 234 of moving optical detector 206 and reference optical detector 210 respectively. Pose processor 214 determines this angle α according to the location of a representation of moving light emitter 212 in an image acquired by reference optical detector 206. For example, when the optical sensor of reference optical detector 206 is a CCD sensor, each pixel in the CCD is associated with an angular step. Thus, angle α is that angular step multiplied by the number of horizontal pixels counted from the optical center of the CCD. It is noted that moving light emitter 212 emits light from the entrance pupil of the optical receptor of moving optical detector 210 (e.g., via a beam splitter).

Pose processor 214 determines the angle γ, between the optical axis of the moving optical detector 210 and Line 238 connecting entrance pupil 232 and entrance pupil 234. Pose processor 214 determines the angle γ according to the location of the representations of reference light emitters $204_1$ and $204_2$ on an image acquired by moving optical detector 210. The optical center of gravity of reference light emitters $204_1$ and $204_2$ is situated at the entrance pupil of the optical receptor of reference optical detector 206.

Pose processor 214 determines the horizontal orientation of moving object 208 by determine the angle between optical axis of the moving optical detector 210 and longitudinal axis 240, designated by the angle β. Orientation processor determines the angle β according to:

$$\beta = \gamma - \alpha \qquad (1)$$

Thus, according to the example brought hereinabove, orientation processor 214 determines the horizontal orientation angle of moving object 208 without determining the position thereof.

As mentioned above, the exemplary method described in conjunction with FIG. 6 is operative when the light emitters emit light from the entrance pupil of the optical receptor and the roll angle is zero. The method may also be operative when the roll angle is substantially small, resulting in an approximation of the azimuth and elevation angles. Alternatively, the method described in conjunction with FIG. 6 is operative in situations wherein the roll angle is known. For example, the two light emitters are situated such that the optical center of gravity thereof is located at that entrance pupil (i.e., the roll angle is known according to the representations of the two light emitters on the opposite optical sensor). In yet another example, the roll angle is known from gravitational tilt sensors. For the exemplary method of FIG. 6 to be operative with the WFOV optical detector described in conjunction with FIGS. 2A, 2B, 3A and 3B, a light emitter is associated with a respective one entrance pupil described therein, and emits light therefrom. Alternatively, at least a pair of light emitters is associated with a respective one entrance pupil and the optical center of gravity thereof is located at that respective entrance pupil. Furthermore, when light is determined as entering through an entrance pupil or pupils, associated with the light emitter or light emitters, the optical tracking system relates to the light emitted by this light emitter or these light emitters (e.g., by selecting the representation of the light emitter or emitters on the opposite optical detector or by enabling these light emitters).

The method described in conjunction with FIG. 6 may be applied when moving object 208 moves in three-dimensions (3D). Accordingly, the orientation of moving object 208 may change in the horizontal, vertical and roll directions. Equation (1) may be applied in both the horizontal and vertical cases. The results of equation (1) are a horizontal orientation angle and a vertical orientation angle. The azimuth and elevation are approximated according to the horizontal orientation, vertical orientation and roll angles. The roll angle may be determined, for example, as mentioned above, according to the representations of the two light emitters on the opposite optical sensor.

According to a further embodiment of the disclosed technique, a reflective surface replaces the reference detector. Thus, the optical tracking system determines the orientation of a moving object, in a reference coordinate system, without determining the position of the moving object. According to this configuration, the optical tracking system includes a light emitter attached to the moving object and a reflective surface situated at a known position in the reference coordinate system. A reflection of the moving light emitter is formed on the fixed reflective surface. When the roll angle is substantially small, the reflection of the moving light emitter is affected only by the change in the azimuth and the elevation angles of the moving object (i.e., yaw and pitch), and not by the translation of the moving object (i.e., there is no parallax). Consequently, the optical tracking system determines the two angle orientation of the moving object according to an image of the reflection of the moving light emitter, acquired by moving light detector. For determining the roll angle (i.e., when accurate values of the azimuth and elevation angles are required), the reflective surface may include additional emitters at the vicinity thereof.

Figure 7:
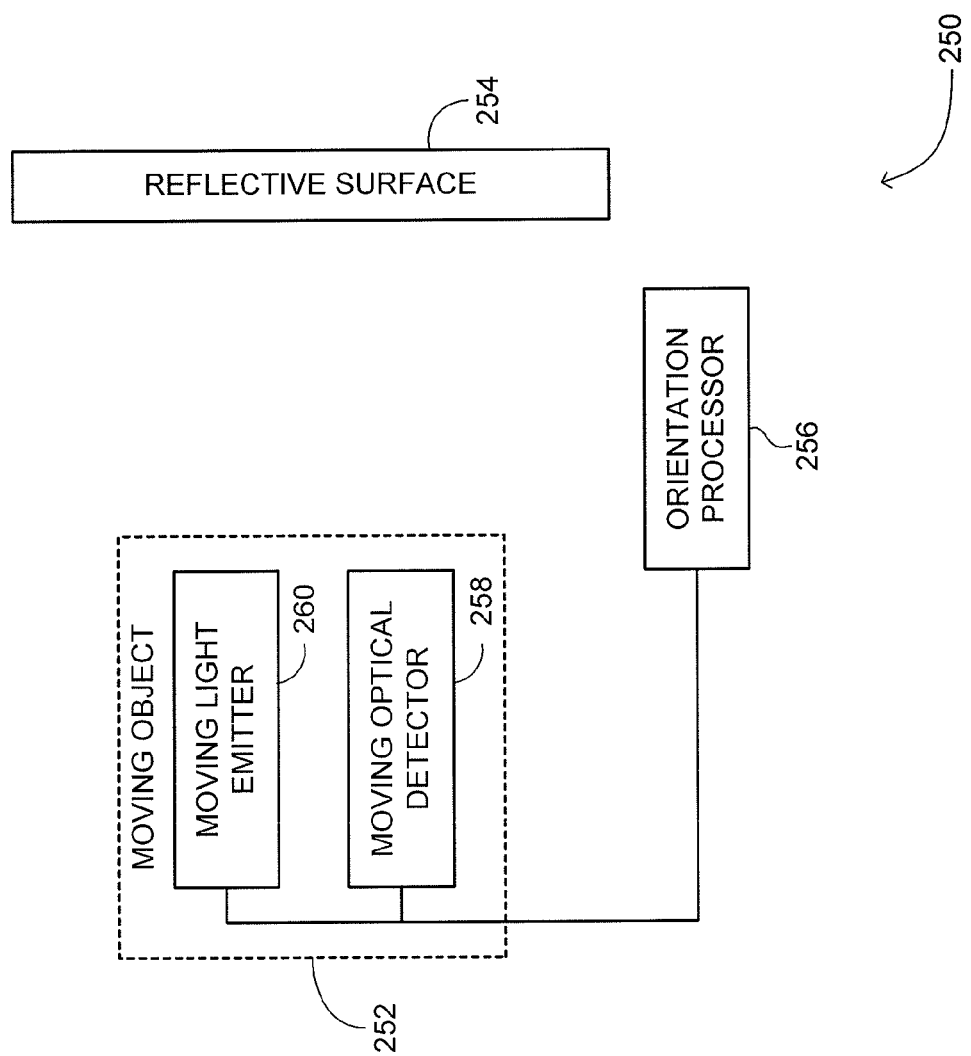
FIG. 7 is a schematic illustration of an optical tracking system, generally reference 250, constructed and operative in accordance with a further embodiment of the disclosed technique.

Reference is now made to FIG. 7, which is a schematic illustration of an optical tracking system, generally reference 250, constructed and operative in accordance with a further embodiment of the disclosed technique. System 250 includes a moving object 252, a reflective surface 254 and an orientation processor 256. Moving object 252 includes a moving optical detector 258 and light emitter 260. Moving optical detector 258 may be a WFOV optical detector as described hereinabove in conjunction with FIGS. 2A and 2B or FIGS. 3A and 3B. Moving optical detector 258 and light emitter 260 are all coupled with orientation processor 256. Light emitter 260 emits light toward reflective surface 254. Reflective surface 254 reflects the light back toward moving WFOV optical detector 258. Reflective surface 254 is, for example, a flat mirror. Reflective surface 254 may further be any surface reflecting the light emitted by Light emitter 260 such as a computer screen, a television screen, a vehicle or aircraft windshield and the like. Reflective surface 254 may be a wavelength selective reflective surface (i.e., reflective surface 254 reflects radiation within a range of wavelengths only). Moving optical detector 258 acquires an image of the reflection of moving light emitter 260. Orientation processor 256 determines the orientation of moving object 252 according to the acquired image of the reflection of light emitter 260. Orientation processor 256 determines the azimuth and elevation angles of the moving object according to the (x, y) location of the light emitter in the image (i.e., when the roll angle is substantially small). However, system 250 described hereinabove in conjunction with FIG. 7, determines the azimuth and elevation angles only. When system 250 is required to determine the roll angle as well, two additional light emitters are fixed, for example, at either side of reflective surface 254. System 250 determines the roll angle according to the position of the two light emitters in the image. Alternatively, a single light emitter of a shape exhibiting rotational asymmetry around an axis normal to the object plane (i.e., where the light emitter is located), within a desired range of roll angles (e.g., an ellipse, an isosceles triangle) is fixed at the vicinity of the reflective surface.

Figure 8:
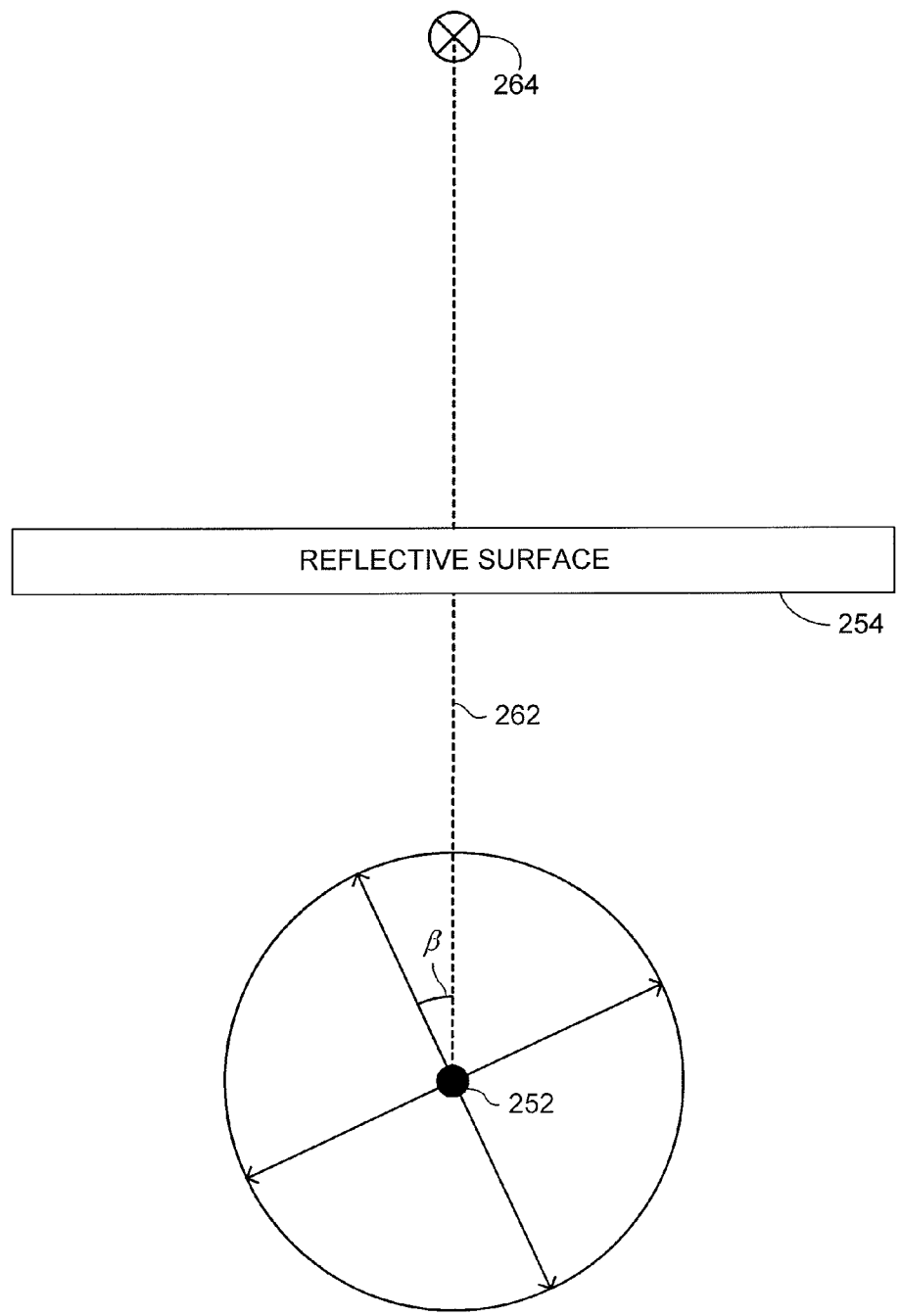
FIG. 8 is a schematic illustration of a two-dimensional example for determining the orientation of a moving object without determining the position thereof in accordance with another embodiment of the disclosed technique.

Reference is now made to FIG. 8, which is a schematic illustration of a two-dimensional example for determining the orientation of a moving object without determining the position thereof in accordance with another embodiment of the disclosed technique and referring back to FIG. 6. Orientation processor 256 determines the orientation of moving object 252, designated by the angle $\beta$, by determining in which angular section of the observed scene mirror image 264 of moving light emitter 260 is situated (i.e., by tracking light incident on the sensor of moving optical detector 258). Orientation processor 256 determines the angle $\beta$ further, according to the location of the projection of mirror image 264 of moving light emitter 260 on moving optical detector 258. As in the example brought hereinabove, when the optical sensor of moving optical detector 258 is a CCD sensor, each pixel in the CCD is associated with an angular step. Thus angle $\beta$ is that angular step multiplied by the number of pixels counted from the optical center of the CCD sensor. As mentioned above, the angle $\beta$ is determined when the roll angle is substantially small.

As mentioned above, a WFOV optical tracking system according to the disclosed technique may be employed in various medical navigation applications and scenarios. For example, a WFOV optical tracking system according to the disclosed technique may be employed for tracking the position and orientation of a medical tool and presenting a real-time representation of the medical tool on an image of a patient. The medical tool may be a hand held tool or a movable tool such as a needle, a real-time imager (e.g., a real-time ultrasound imager, a real time X-ray imager located on a C-arm), a stylus, a surgical knife, a catheter and the like. In general, the medical WFOV optical tracking system according to the disclosed technique, determines the position and orientation of at least one target object in a reference coordinate system. Such a system generally includes at least three light emitters and at least one optical detector which can be a WFOV optical detector. The WFOV optical detector is similar to as described above in conjunction with FIGS. 2A, 2B, 3A and 3B. The reference location is associated with a reference coordinate system. Each optical detector and each light emitter is adapted to be attached to a respective one of at least one target object and a reference location. Each optical detector acquires an image of the light emitter or light emitters within the field of view thereof. Furthermore, each of the light emitters is within the field of view of at least one of the optical detector or detectors. A processor determines the position and orientation of the target object in the reference coordinate system, according to the representations of the light emitters (i.e., as determined either by the optical detector which acquired the image or by the processor both as explained above in conjunction with FIG. 4) similar to as described above in conjunction with FIG. 4.

The above mentioned medical WFOV optical tracking system may exhibit various configurations. According to one exemplary configuration, the medical WFOV optical tracking system includes a WFOV optical detector and at least three light emitters. The WFOV optical detector is attached to a target object and the three light emitters are attached to the reference location or vice versa. According to another exemplary configuration, the medical WFOV optical tracking system includes a WFOV optical detector, another optical detector and at least three light emitters. The WFOV optical detector is attached to the target object and the other optical detector is attached to the reference location (or vice versa). One light emitter is attached to target object and two light emitters are attached to the reference location (or vice versa).

In general there can be more than one target object. Each pair consisting of the reference location and a target object is associated with at least three light emitters, each attached to either the target object or the reference location employed for determining the position and orientation of the target object. The above mentioned target object or objects and the reference location are respective elements in a tuple including at least two elements from a group consisting of a display (e.g., Head Mounted Display—HMD) further explained below, a patient body location, a medical tool, a physician body location, and a fixed position. Following are various examples for such a tuple of elements including at least two elements: {display, medical tool}, {fixed position, medical tool}, {display, medical tool, medical tool}, {display, medical tool, fixed position}, {display, patient body location, medical tool}, {fixed position, medical tool, medical tool}, {fixed position, patient body location, medical tool}, {patient body location, medical tool, physician body location}, {fixed position, patient body location, medical tool, physician body location}, {display, fixed position, patient body location, medical tool}, {display, patient body location, medical tool, medical tool}, {tool, tool}, and {patient body location, patient body location}. The tuple {tool, tool} refers to two different medical tools (i.e., the target object or objects and the reference location are all medical tools). The tuple {body part of patient, body part of patient} refers to two different patient body locations (e.g., thigh and leg). Each optical detector and each light emitter is attached to a respective one of the elements. Furthermore, each element may be designated as the reference location according to particular needs and the remaining elements are designated as target objects. The above mentioned fixed position may be for example, the wall or the ceiling of an operating room. Alternatively, the fixed position may be a mechanical support (e.g., a tripod, a mechanical arm), which is stationary during part of the medical procedure and may be moved between parts of the procedure. Furthermore, each of the above elements may be associated with a respective coordinate system. These respective coordinate systems may be registered with each other and with the reference coordinate system.

As mentioned above, medical optical tracking system according to the disclosed technique may include a display. The display displays a model representing information relating to the patient. The display may also display real-time image of the patient, such as real-time ultrasound images, real-time X-ray images (e.g., acquired with X-ray imager located on a C-Arm), laparoscopy images and real-time MRI images. The display may further display representations relating to medical tools as well as navigational information (e.g., marks representing target locations or the trajectory of medical tool). The display may be, for example, a 2D or 3D screen display (e.g., LED display, LCD display, plasma display or Cathode Ray Tube—CRT display), a hand-held display (e.g., a tablet computer), or a Head Mounted Display (HMD) as further explained below. The model is, for example, a two dimensional (2D) or a three dimensional (3D) image of the patient (e.g., X-Ray image, CT model, MRI model). Alternatively, the model may be a symbolic model or a virtual model representing the body of the patient or various regions thereof (e.g., the heart, the brain or the uterus, tumor within the body, the circulatory system or parts thereof). The model and the navigational information is associated with the reference coordinate system. When the model is an image, the coordinate system associated with the image is registered with the reference coordinate system as further explained below.

Figure 9:
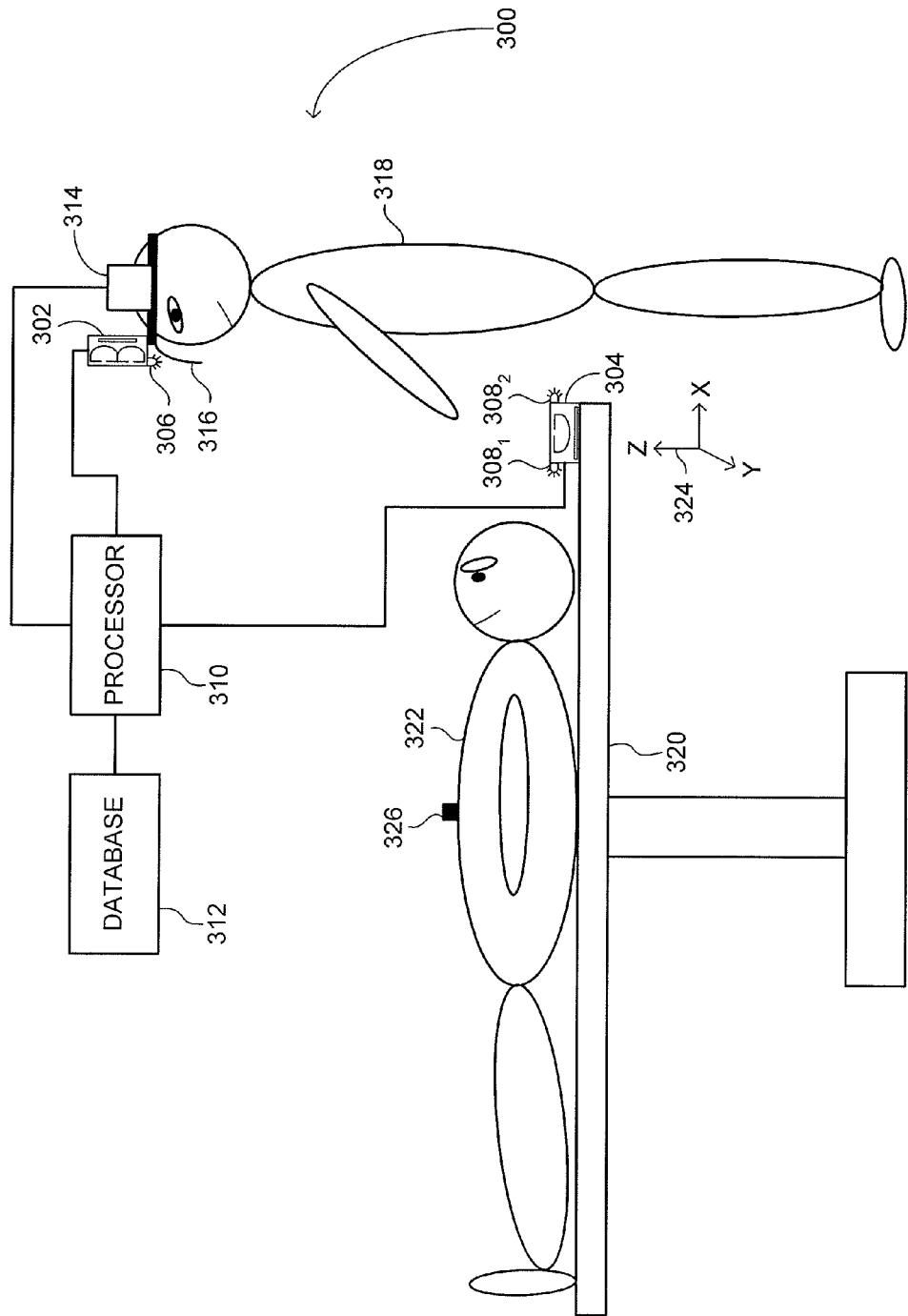
FIG. 9 is a schematic illustration of an exemplary medical WFOV medical tracking system, in accordance with a further embodiment of the disclosed technique.

The description herein below, in conjunction with FIGS. 9, 10, 11, 12, 13, and 14 present various examples of several of the above described medical WFOV optical tracking systems. According to a first example, the medical WFOV optical tracking system according to the disclosed technique may be employed for presenting a model of a patient to a physician at an orientation and scale corresponding to the point of view of the physician. Reference is now made to FIG. 9, which is a schematic illustration of an exemplary medical WFOV tracking system, generally reference 300, in accordance with a further embodiment of the disclosed technique. System 300 includes a WFOV optical detector 302, another optical detector 304, at least one light emitter 306, at least two other light emitters $308_1$ and $308_2$, a processor 310, a database 312 and a display such as Head Mounted Display (HMD) 314. HMD 314 includes a visor 316. Alternatively HMD 314 may be in the form of a near-to-eye display (i.e., displays located close to the eye such as Google glass and the like).

Processor 310 is coupled with database 312, WFOV optical detector 302, HMD 314, optical detector 304. When light emitter 306, light emitters $308_1$ and $308_2$ are light sources such as LEDs, processor 310 is optionally coupled with light emitter 306 and with light emitters $308_1$ and $308_2$. Light emitter 306 is attached to WFOV optical detector 308 and both are attached to HMD 314. HMD 314 along with WFOV optical detector 308 and light emitter 306 are donned by a physician 318. Alternatively, light emitter 306 may be directly attached to HMD 314. Optical detector 304 is firmly attached to a treatment bed 320 on which a patient 322 lies. System 300 is associated with a reference coordinate system 324 which, in this case, is also the coordinate system associated with optical detector 304. However, reference coordinate system 324 may alternatively be the reference coordinate system of, for example, HMD 314.

Database 312 stores a model of the body of patient 322 or parts thereof (e.g., the head, the torso). This model may be 3D model such as a symbolic or a virtual model. Alternatively, the model is a 3D model such as a Computer Tomography (CT) model or a Magnetic Resonance Imaging (MRI) model. The model is associated with reference coordinate system 324. When the model is an image, the coordinate system associate with the image is registered with reference coordinate system 324 (i.e., each position in the coordinate system associate with the image has a corresponding position in reference coordinate system 324). This registration is achieved, for example, by employing image processing techniques to determine the position of a fiducials, such as fiducial 326, which is also visible in the image, in the coordinate system associate with the 3D image. Then, the location of fiducial 326 is determined in reference coordinate system 324, for example by employing a stylus fitted with a WFOV optical detector as further explained below. Thus, a correspondence between the location of the fiducial in coordinate system 324 and in the coordinate system associated with the image. To register, for example, two 3D coordinate systems, the position and orientation of at least three common distinct features should be determined in both coordinate systems. The distinct features may also be distinct features on the body of patient 322, such as the nose bridge, the medial cantus or the tragus. Processor 310 then determines the transformation between the two coordinate systems.

One exemplary use of system 300 may be for marking incision marks on a patient employing a 3D image of the patient. To that end, patient 322 lies on treatment bed 320. WFOV optical detector 302 and optical detector 304 acquire an image or images of the light emitters within the FOV thereof. In FIG. 9, WFOV optical detector 302 acquires an image or images of light emitters $308_1$ and $308_2$ and optical detector 304 acquires an image of light emitter 306. Processor 310 determines the position and orientation of WFOV optical detector 302 relative to optical detector 304, and consequently in reference coordinate system 324, according to the representation of light emitter $308_1$ and $308_2$ and light emitter 306 (i.e., as determined from the acquired images either by WFOV optical detector 302 and optical detector 304 respectively or by processor 310). Thus processor 310 determines the position and orientation of the head of physician 318 in reference coordinate system 324. Since the 3D image is registered with reference coordinate 324, processor 310 renders the 3D image such that HMD 314 displays the 3D image on visor 316 at the scale and orientation corresponding to the determined position and orientation (i.e., the point of view) of physician 318. Physician 318 can view internal parts of patient 322 and, for example, mark incision marks on patient 322 which are suitable for the required procedure. It is noted that, when HMD 314 displays an image on visor 316, processor 310 may further have to adjust the orientation of the image to account for the angle between the optical center of the visor and optical detector 316 attached to HMD 314. Since WFOV optical detector 302 is attached to HMD 314, this angle is fixed and needs to be determined only once.

Figure 10:
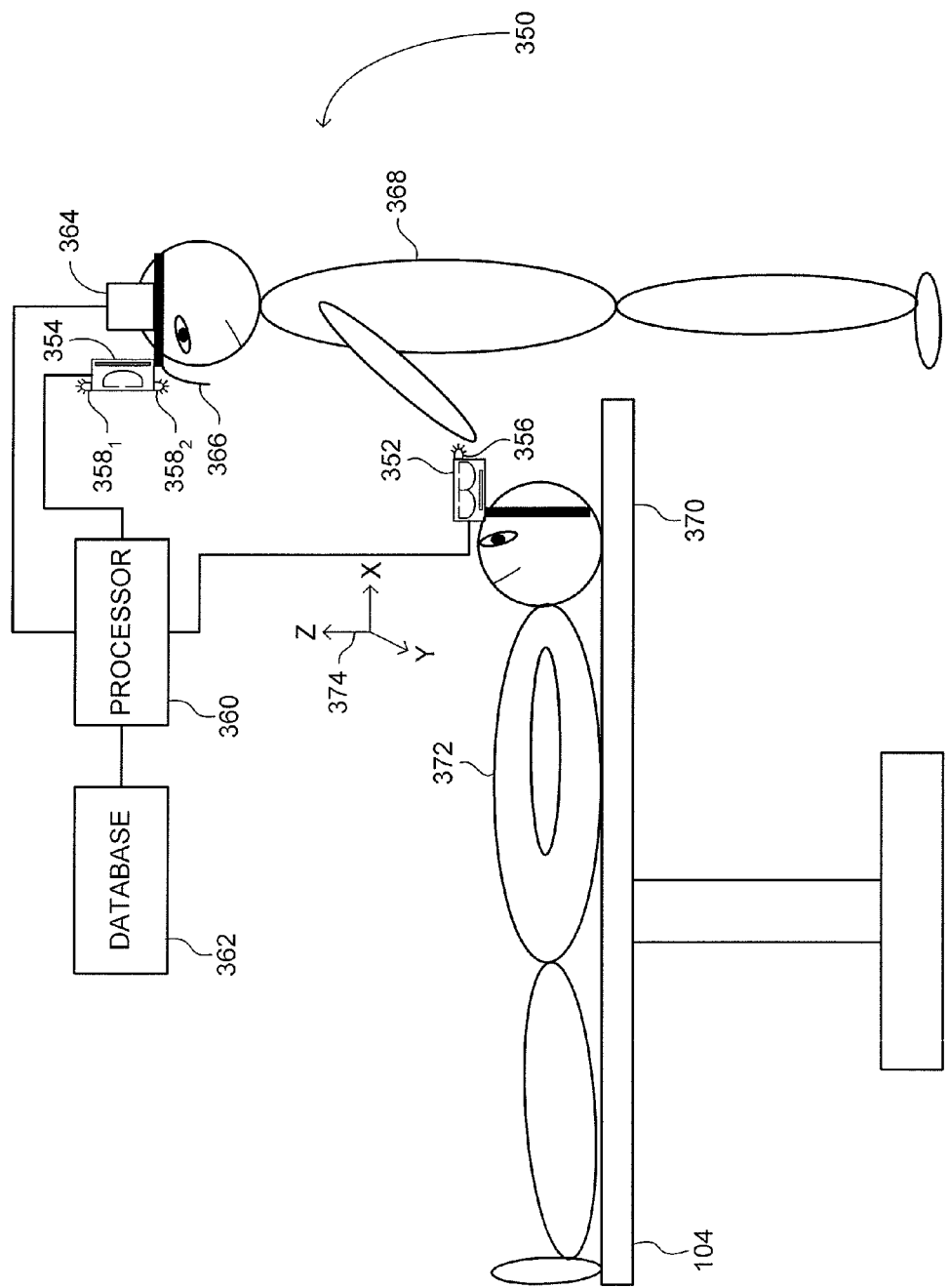
FIG. 10 is a schematic illustration of an exemplary medical WFOV medical tracking system, in accordance with another embodiment of the disclosed technique.

In the above description of system 300, the patient must remain stationary for the superposition of the model on the patient to be correctly maintained. However, according to another example, a detector is placed on the patient and the relative position and orientation of between the two detectors (i.e., and thus between the head of the physician and the patient) is determined. Furthermore, similar to as described above in conjunction with FIG. 9, the model is associated with the reference coordinate system. When the model is a 3D image, the coordinate system associated with the 3D image is registered with the coordinate system associated with the detector placed on the patient. Thus, the patient may move and the 3D image shall move therewith, thereby maintaining the correct perspective of the image for the physician. Reference is now made to FIG. 10, which is a schematic illustration of an exemplary medical WFOV tracking system, generally reference 350, in accordance with another embodiment of the disclosed technique. System 350 includes a WFOV optical detector 352, another optical detector 354, at least one light emitter 356, at least two other light emitters $358_1$ and $358_2$, a processor 360, a database 362 and a display such as HMD 364. HMD 364 includes a visor 366. HMD 364 may also be in the form of goggles.

Processor 360 is coupled with database 362, WFOV optical detector 352, HMD 364 and with optical detector 354. When light emitter 356, light emitters $358_1$ and $358_2$ are LEDs processor 360 is optionally coupled with light emitter 356 and with light emitters $358_1$ and $358_2$. Light emitter 356 is attached to WFOV optical detector 352 and both are attached to a body location of patient 372 (i.e., either directly or attached to a fixture which is attached to a body location of patient 372, such as the head, a limb or the jaw). HMD 364 along with optical detector 354 and light emitters light emitter $358_1$ and $358_2$ are attached to the head of a physician 368. Alternatively, light emitters $358_1$ and $358_2$ may be directly attached to HMD 364. System 350 is associated with a reference coordinate system 374 which, in this case, is also the coordinate system associated with WFOV optical detector 352.

Similar to database 312 (FIG. 9), Database 362 stores a model patient 372 or of a part thereof. When the model is an image (i.e., a 2D image or a 3D image), the coordinate system associate with the image is registered with reference coordinate system 374. Similar to system 300 (FIG. 9), system 350 may be employed, for example, for marking incision marks on a patient employing a 3D image of the patient. To that end, patient 372 lies on treatment bed 370. WFOV optical detector 352 and optical detector 354 acquire an image or images of the light emitters within the FOV thereof.

In FIG. 10, WFOV optical detector 352 acquires an image or images of light emitters $358_1$ and $358_2$ and optical detector acquire 354 acquire an image of light emitter 356. Processor 360 determines the relative position and orientation of WFOV optical detector 352 relative to optical detector 354, and consequently in reference coordinate system 374 (i.e., the relative position and orientation between optical detector 354 and WFOV optical detector 352 and thus between patient 372 and the head of physician 368) according to the representation of light emitter 356 and the representations of light emitters $358_1$ and $358_2$ (i.e., as determined from the acquired images either by optical detector 354 and optical detector 352 respectively or by processor 360). Similar to as described above in conjunction with FIG. 9, since the 3D image is registered with reference coordinate 374, processor 360 renders the 3D image such that HMD 364 displays the 3D image on visor 366 at the scale and orientation corresponding to the determined relative position and orientation between WFOV optical detector 352 (i.e., the patient) and optical detector 354 (i.e., the physician). Thus, in the event that either patient 372 and physician 368 move one with respect to the other, the perspective of 3D image presented to physician 368 shall be adjusted accordingly and shall appear superimposed on the body of patient 372. Physician 368 can view internal parts of patient 372 and mark incision marks on patient 372 which are suitable for the required procedure. Similar to as mentioned with regards to system 300 (FIG. 9), when HMD 364 displays an image on visor 366, processor 310 may further have to adjust the orientation of the image to account for the angle between the optical center of the visor and optical detector 354 attached to HMD 364. Since optical detector 354 is attached to HMD 364, this angle is fixed and needs to be determined only once. One particular advantage of the medical WFOV optical tracking system described in conjunction with FIG. 10 is the freedom of motion provided for physician 368 to move around patient 372 without losing track.

Figure 11:
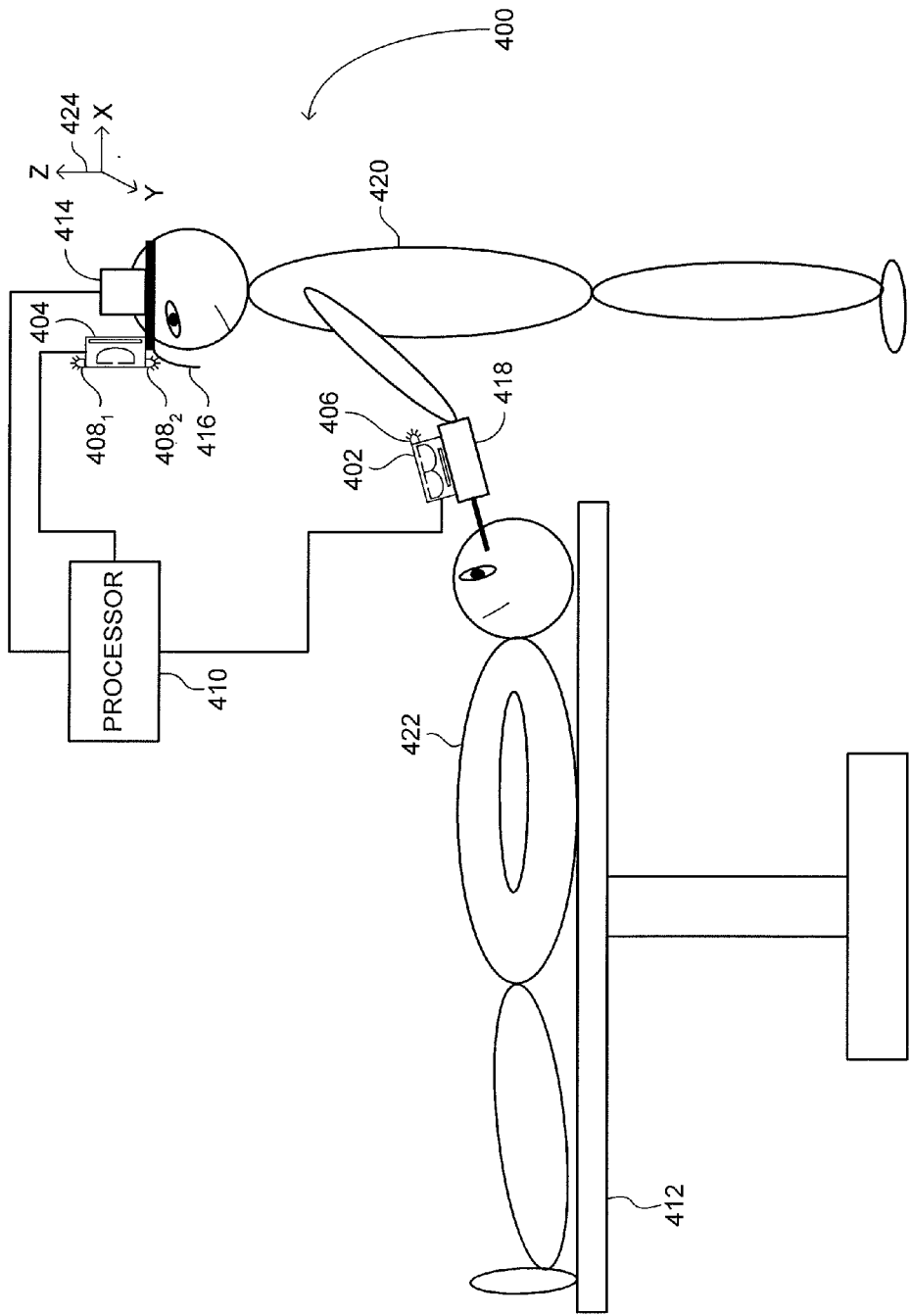
FIG. 11 is a schematic illustration of an exemplary medical WFOV medical tracking system, in accordance with a further embodiment of the disclosed technique.

The medical WFOV optical tracking system according a further embodiment of the disclosed technique may be employed for tracking the position and orientation of a medical tool and for guiding a medical tool during a medical procedure. Reference is now made to FIG. 11, which is a schematic illustration of an exemplary medical WFOV tracking system, generally reference 400, in accordance with a further embodiment of the disclosed technique. System 400 is used for tracking a medical tool in a reference coordinate system. System 400 includes a WFOV optical detector 402, another optical detector 404, at least one light emitter 406, at least two other light emitters $408_1$ and $408_2$, a processor 410 and a display such as HMD 414. HMD 414 includes a visor 416. HMD 414 may also be in the form of near-eye-display.

Processor 410 is coupled with WFOV optical detector 402, HMD 414, optical detector 404. When light emitter 406 and light emitters $408_1$ and $408_2$ are LEDs, processor 310 is optionally coupled with light emitter 406 and light emitters $408_1$ and $408_2$. Light emitter 406 is attached to WFOV optical detector 402 and both are attached to medical tool 418. Light emitter $408_1$ and $408_2$ are attached to optical detector 404 and both are attached to HMD 414. HMD 414 along with optical detector 404 and light emitters $408_1$ and $408_2$ are attached to the head of a physician 420. Alternatively, light emitters $408_1$ and $408_2$ may be directly attached to HMD 414. System 400 is associated with a reference coordinate system 424 which, in this case, is also the coordinate system associated with optical detector 404. Medical tool 418 is, for example, an ultrasound imager, a medical knife, a catheter, a laparoscope or a medical stylus used by a physician 420 during a procedure conducted on a patient 422. Medical tool 418 is tracked in a reference coordinate system 424 associated with system 400. In FIG. 10 reference coordinate system 424 is also the coordinate system associated with detector 404.

System 400 may be employed for tracking medical tool 418 even when part thereof may be concealed. Furthermore, System 400 may also be employed for presenting data acquired by medical tool 418 at the location from which that data was acquired. For example, when medical tool 418 is a medical needle (e.g., a biopsy needle) inserted into patient 422 lying on treatment bed 412, portions of medical tool 418 may be obscured to physician 400.

To that end WFOV optical detector 402 and optical detector 404 acquire an image or images of the light emitters within the FOV thereof. In FIG. 11, WFOV optical detector 402 acquires an image or images of light emitters $408_1$ and $408_2$ and optical detector acquire 404 acquire an image of light emitter 406. Processor 410 determines the relative position and orientation between WFOV optical detector 352 (i.e., the tool) and optical detector 354 (i.e., the physician) according to representations of light emitters $408_1$ and $408_2$ and the representation of light emitter 406 (i.e., as determined from the acquired images either by WFOV optical detector 402 and optical detector 404 respectively or by processor 510). Furthermore, processor 410 constructs a visual representation (not shown) of the medical tool 418 or at least of the obscured portion of thereof, for example according to known dimensions of medical tool 418 and the known spatial relationship between WFOV optical detector 402 and medical tool 418. The spatial relationship between WFOV optical detector 402 and medical tool 418 is determined, for example, during the manufacturing process thereof. Medical tool 418, along with the visual representation thereof, is presented by HMD 414 on visor 416 to physician 420. Accordingly, physician 420 can view the location of the obscured portion of medical tool 418 within the body of patient 422. When medical tool 418 is an ultrasound imager, the image produced by the ultrasound imager may be displayed to physician 420 superimposed on the location in the body of patient 422 at which the image was acquired. Similar to as mentioned with regards to system 300 (FIG. 9), when HMD 414 displays an image on visor 416, processor 410 may further have to adjust the orientation of the image to account for the angle between the optical center of the visor and optical detector 404 attached to HMD 414. Since optical detector 404 is attached to HMD 414, this angle is fixed and needs to be determined only once. One particular advantage of the medical WFOV optical tracking system described in conjunction with FIG. 11 is the freedom of motion provided for physician 368 to move tool 418 to various positions and orientations without losing track.

According to another example, a medical WFOV optical tracking system may be employed for tracking the position and orientation of a medical tool in cases where the tool is obscured even when the patient moves. Additionally or alternatively, the medical WFOV optical tracking system according to the disclosed technique may further be employed for tracking the position and orientation of a medical tool, superimposed on a model (i.e., a symbolic or virtual model, or a 2D or a 3D image) of the patient. Thus, the physician may view and guide the medical tool toward a target location within the patient.

Figure 12:
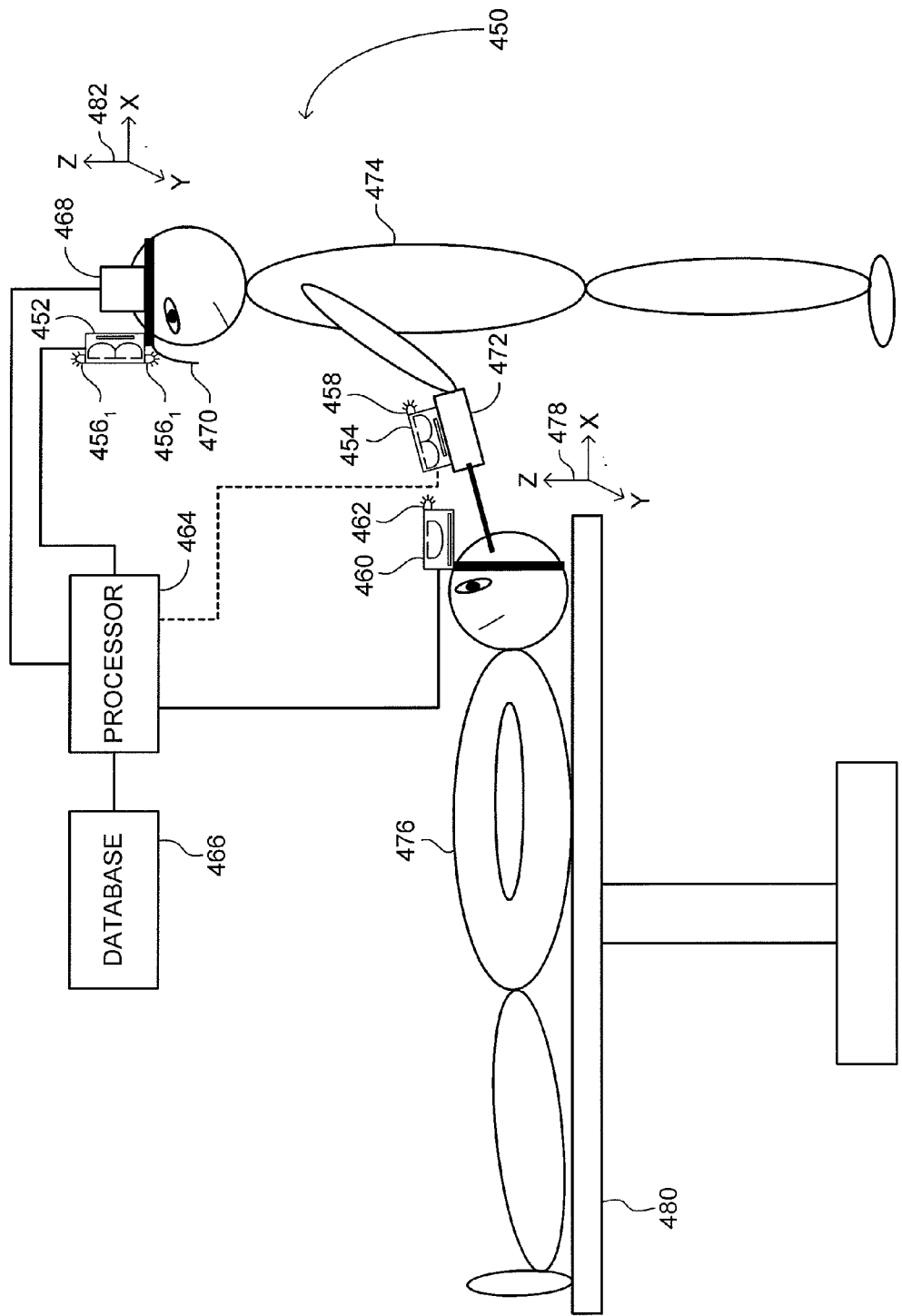
FIG. 12 is a schematic illustration of an exemplary medical WFOV medical tracking system, in accordance with another embodiment of the disclosed technique.

Reference is now made to FIG. 12, which is a schematic illustration of an exemplary medical WFOV tracking system, generally reference 450, in accordance with another embodiment of the disclosed technique. System 450 is used for tracking a medical tool in a reference coordinate system, superimposed on a model of a patient. System 450 includes a first WFOV optical detector 452, a second WFOV optical detector 454, another optical detector 460, two light emitters $456_1$ and $456_2$, first light emitter 458 and second light emitter 462. System 450 further includes a processor 464, a database 466 and a display such as HMD 468. HMD 468 includes a visor 470. HMD 468 may also be in the form of near-eye-display.

Processor 464 is coupled with database 466, first WFOV optical detector 452, HMD 414, optical detector 460 and. Processor 464 is further wirelessly coupled with second WFOV optical detector 454 as indicated by the dashed line in FIG. 12. When light emitters $456_1$ and $456_2$ and light emitter 462 are LEDs, processor 464 is optionally coupled therewith. When light emitter 458 is a LED, processor 464 is also optionally wirelessly coupled therewith. HMD 468 along with first WFOV optical detector 452 and light emitter $456$ is donned by a physician 474. Light emitter 458 is attached to second WFOV optical detector 454 and both are attached to medical tool 472. Light emitter 460 is attached to optical detector 460 and all are attached to the head of patient 476 (i.e., the patient body location is the head) lying on treatment bed 480. System 400 is associated with a reference coordinate system 478 which, in this case, is also the coordinate system associated with optical detector 460. Furthermore, HMD 468 is associated with a respective coordinate system 482. Similar to medical tool 418 (FIG. 11), medical tool 472 is, for example, an ultrasound imager, a medical knife, a catheter, a laparoscope or a medical stylus used by a physician 474 during a procedure conducted on a patient 476.

System 450 may be employed for tracking medical tool 472 by superimposing a representation of medical tool 472 on a model (i.e., a symbolic or virtual model or a 3D image) of a patient 476. Furthermore, similar to system 400 described above in conjunction with FIG. 11, system 450 may also be employed for presenting data acquired by medical tool 472 at the location from which that data was acquired. To that end, the coordinate system of the model is associated with reference coordinate system 478. When the model is an image of the patient, the coordinate system of the image is registered with reference coordinate system 478 (e.g., as described above in conjunction with FIG. 9).

First WFOV optical detector 452, second WFOV optical detector 454 and optical detector 456 all acquire an image or images of the light emitters within the FOV thereof. In FIG. 12, first WFOV optical detector 452 acquires an image or images of first light emitters 458 and of second light emitter 462. Second WFOV optical detector 454 and optical detector 460 both acquire an image or images of light emitters $456_1$ and $456_2$. Furthermore, second WFOV optical detector 454 may also acquire an image of light emitters 462 and optical detector 460 may also acquire an image of light emitter 458.

Processor 464 synchronizes the operation of first WFOV optical detector 452, of second WFOV optical detector, of optical detector, of light emitters $456_1$ and $456_2$, of light emitter 458 and of light emitter 462 such that the time period when first WFOV optical detector 452 acquires an image of light emitter 458 and second WFOV optical detector 454 acquires an image of light emitters $456_1$ and $456_2$, does not overlap with the time period when first WFOV optical detector 452 acquires an image of light emitter 462 and optical detector 460 acquires an image of light emitters $456_1$ and $456_2$. In other words, the operation of the pair of detectors including first WFOV optical detector 452 and second WFOV optical detector 454 and of light emitters $456_1$, $456_2$ and 458 is mutually exclusive in time with respect to the operation of the pair of detectors including first WFOV optical detector 452 and optical detector 460 and of light emitters $456_1$, $456_2$ and 460

Processor 464 determines the position and orientation of first WFOV optical detector 452 in reference coordinate system 478 and consequently of HMD 468 relative to the head of patient 476, according to the representation of light emitter 462 and the representations of light emitters $456_1$ and $456_2$ (i.e., as determined either by first WFOV optical detector 452 and optical detector 460 respectively or by processor 464). Also, processor 464 determines the position and orientation of optical detector 454 in coordinate system 482 respective of HMD 468 and consequently the position and orientation of medical tool 472 relative to HMD 468, according to the representation of light emitter 458 and the representations of light emitters $456_1$ and $456_2$ (i.e., as determined by either first WFOV optical detector 452 and second optical detector 454 respectively or by processor 464). Processor 464 may further synchronize second WFOV optical detector 454 and optical detector 460 with light emitters 458 and 462, and employ the representations of light emitter 462 acquired by second WFOV optical detector 454 and of light emitter 458 acquired by optical detector 460 to verify the correctness of the determined position and orientation of second WFOV optical detector 454 relative to optical detector 460.

According to the determined relative positions and orientations between medical tool 472, HMD 468 and patient 476, processor 464 may render the model of patient 476 in the correct perspective and provide the rendered model to HMD 468 and optionally, superimpose a representation of medical tool 472, at the corresponding position and orientation relative to the HMD 468. Furthermore, processor 464 may superimpose navigational information on the model. This navigational information is, for example, a mark representing a target location, a line representing the trajectory (including projected trajectory) of medical tool 472, marks representing the fiducial markers used for the registration. Processor provides HMD 468 with the rendered 3D image superimposed with a representation of medical tool 472 and with the navigational information. HMD 468 displays this rendered and superimposed image to physician 474 on visor 470. Additionally, since processor 464 determines the relative position and orientations between first WFOV optical detector 452, second WFOV optical detector 454 and optical detector 460, even when patient 476 moves, the model, the representation of medical tool 472 and the navigation information shall be adjusted to the new point of view of physician 474. HMD 468 may display only one of the model of a patient, representation of medical tool 472 and navigational information or any pair thereof.

Similar to as mentioned with regards to system 300 (FIG. 9), when HMD 468 displays an image on visor 470, processor 464 may further have to adjust the orientation of the presented image to account for the angle between the optical center of the visor and first WFOV optical detector 452 attached to HMD 468. Since first WFOV optical detector 452 is attached to HMD 468, this displacement is fixed and needs to be determined only once. It is also noted that system 450 may be modified to include two or more WFOV optical detectors attached to any of HMD 468 or medical tool 472, thus further increasing the FOV of tracking system 450. Similarly, system 450 may be modified to include two or more optical detectors attached to the patient. One particular advantage of the medical WFOV optical tracking system described in conjunction with FIG. 12 is the freedom of motion provided for physician 474 to move tool 472 to various positions and orientations and for physician 474 to move around patient 476 without losing track.

Figure 13:
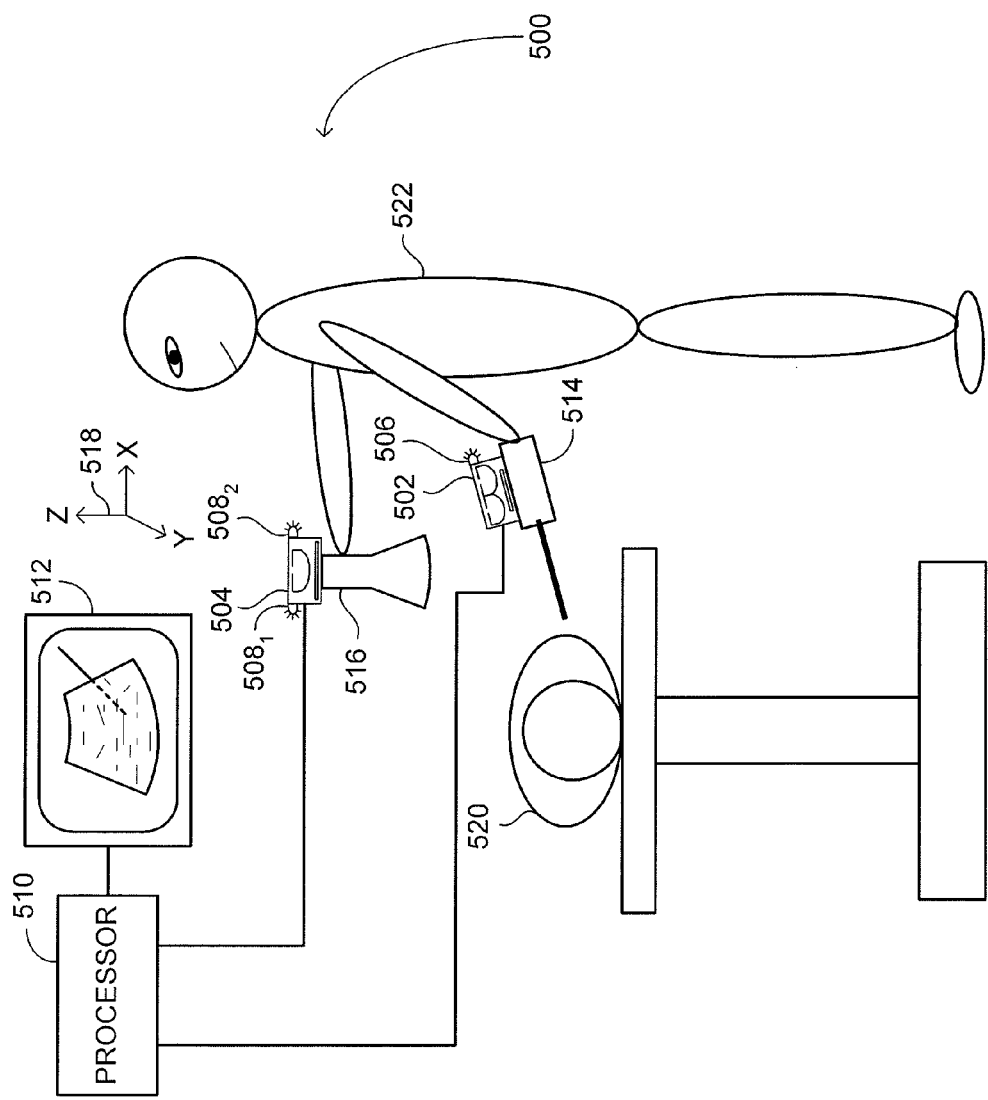
FIG. 13 is a schematic illustration of an exemplary medical WFOV medical tracking system, in accordance with a further embodiment of the disclosed technique.

Reference is now made to FIG. 13, which is a schematic illustration of an exemplary medical WFOV tracking system, generally reference 500, in accordance with a further embodiment of the disclosed technique. System 500 is employed for tracking one medical tool with respect to another medical tool. System 500 includes a WFOV optical detector 502, another optical detector 504, at least one first light emitter 506, and at least two other light emitters $508_1$ and $508_2$. System 450 further includes a processor 510 and a display 512.

Processor 510 is coupled with WFOV optical detector 502, with second optical detector 504. When first light emitter 506 and two other light emitters $508_1$ and $508_2$ are LEDs, processor 510 is optionally coupled therewith. Light emitter 506 is attached to WFOV optical detector 502 and both are attached to a first medical tool 512 which, in FIG. 13 is exemplified as a needle (e.g., a biopsy needle or an amniocentesis needle). Light emitters $508_1$ and $508_2$ are attached of second optical detector 504 and all are attached to a second medical tool 514. Second medical tool 514 may be, for example, any real-time imaging device which, in FIG. 13 is exemplified as an ultrasound imager. However, second medical tool 514 may alternatively be a laparoscopy camera, an X-ray imager located on a C-arm or a real-time MRI imager. System 500 is associated with a reference coordinate system 518 which, in this case, is also the coordinate system associated with optical detector 504. With regards to the above examples of real-time imagers, the relative angle, and in some cases also the relative position, between the images produced by these real-time imagers and the optical detector attached thereto should be determined prior to use.

System 500 is used for tracking first medical tool 514 relative to second medical tool 516 and present on display 512 information related to both tools, at the correct spatial relationship there between. For example, when first medical tool 514 is a needle and second medical tool 516 is an ultrasound imager, ultrasound imager 516 acquires a real time image or images of a region of interest of the body of patient 520 (e.g., the abdomen, the embryo). A physician 522 inserts needle 514 toward the region of interest.

WFOV optical detector 502 and optical detector 504 acquire an image or images of the light emitters within the FOV thereof. In FIG. 13, WFOV optical detector 502 acquires an image or images of light emitters $508_1$ and $508_2$ and optical detector acquire 504 acquire an image of light emitter 506. Processor 510 determines the position and orientation of WFOV optical detector 502 relative to optical detector 504, and consequently in reference coordinate system 518, according to the representations of light emitters $508_1$ and $508_2$ and the representation of light emitter 506 (i.e., as determined from the acquired images either by WFOV optical detector 502 and optical detector 504 respectively or by processor 510). Thus processor 510 determines the position and orientation of the needle 514 relative to ultrasound imager 516. Display 512, displays the acquired ultrasound image along with a representation of needle 514 and optionally with a representation of the projected path of needle 514 in the region of interest, superimposed on the acquired image.

It is noted that an additional optical detector, which may be a WFOV optical detector, and an additional light emitter may both be located, for example of the head of physician 522. Processor 510 then determines the relative position and orientation between the head of the physician and medical tool 516. Thus, when medical tool 516 is for example an ultrasound imager, processor 510 may render the ultrasound image such that display 512 displays the ultrasound image at the orientation corresponding to the point of view of physician 522

Figure 14:
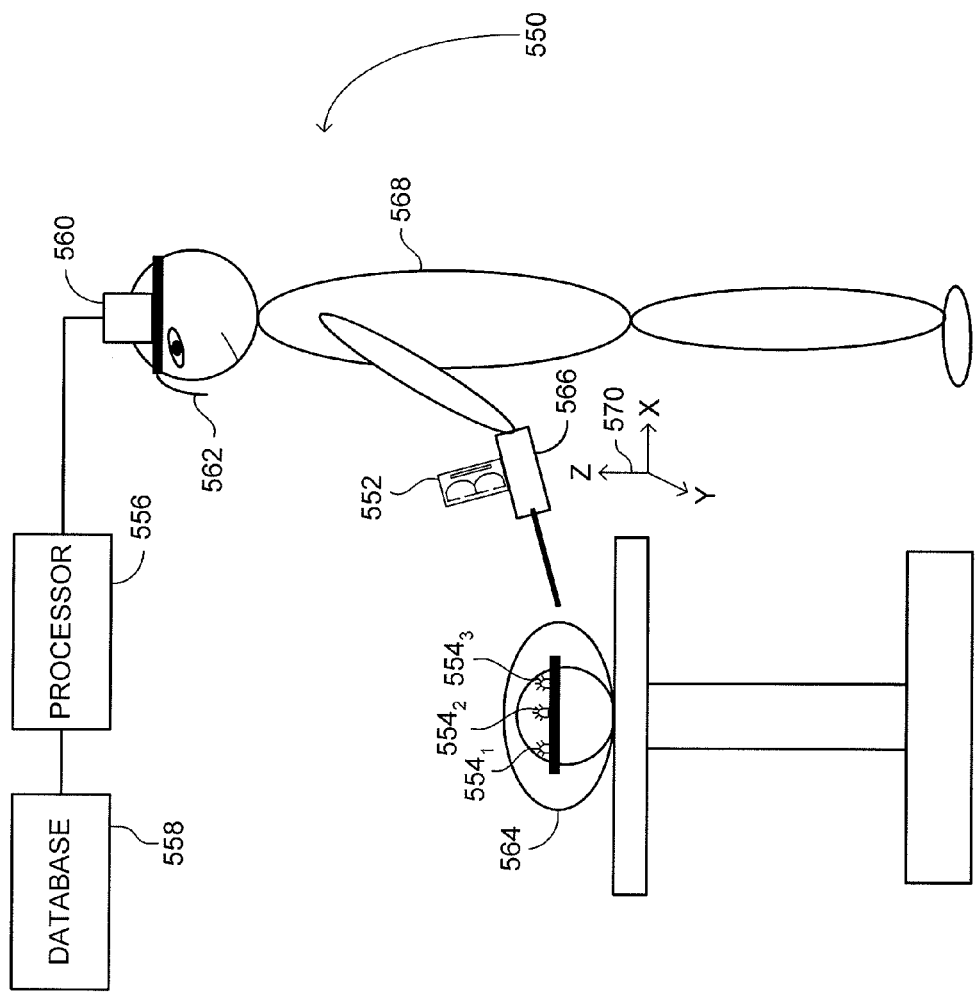
FIG. 14 is a schematic illustration of an exemplary medical WFOV medical tracking system, in accordance with another embodiment of the disclosed technique.

Reference is now made to FIG. 14, which is a schematic illustration of an exemplary WFOV medical tracking system, generally reference 550 in accordance with another embodiment of the disclosed technique. System 550 includes a WFOV optical detector 552, at least three light emitters $554_1$, $554_2$ and $554_3$, a processor 556, a database 558 and a display such as Head Mounted Display (HMD) 560. HMD 560 includes a visor 562. Alternatively HMD 314 may be in the form of near-eye-display.

Processor 556 is coupled with database 558, WFOV optical detector 552, HMD 560. When light emitters $554_1$, $554_2$ and $554_3$ are LEDs, processor 556 is optionally coupled therewith. Light emitters $554_1$, $554_2$ and $554_3$ are attached to a body location of patient 564 and WFOV optical detector is attached to a medical tool 566 held by a physician 568. System 550 is associated with a reference coordinate system 570, which in this case is also the coordinate system associated with patient 564.

System 550 may be employed for tracking medical tool 566 relative to patient 564. System 550 may also be employed for presenting data acquired by medical tool 566 at the location from which that data was acquired. To that end WFOV optical detector 552 acquires an image or images of light emitters $554_1$, $554_2$ and $554_3$ within the FOV thereof. Processor 566 determines the relative position and orientation between WFOV optical detector 552 (i.e., the tool) and the patient according to the representations of light emitters $554_1$, $554_2$ and $554_3$ (i.e., as determined either by WFOV optical detector 552 or by processor 566). Furthermore, processor 556 may further constructs a visual representation (not shown) of the medical tool 566 or at least of the obscured portion of thereof. Medical tool 566, along with the visual representation thereof, is presented by HMD 560 on visor 562 to physician 568. Accordingly, physician 568 can view the representation of medical tool 566 superimposed on a model of patient 564. When medical tool 566 is an ultrasound imager, the image produced by the ultrasound imager may be displayed to physician 568 superimposed on a model of patient 564 corresponding to the location in the body of patient 564 at which the image was acquired. When medical tool 566 is a four dimensional (4D) ultrasound transducer (i.e., acquiring a live 3D image), the live 3D ultrasound image may be displayed. Additionally, a 3D ultrasound model can be built based upon regular 2D ultrasound images, each taken at different positions and orientations in the coordinate system associated with patient 564.

As mentioned above, the display employed in any of the above WFOV medical tracking systems may a hand held display which includes a camera. The relative position and orientation between the hand held display and the patient can be tracked (e.g., the hand held device is one of the target objects). Furthermore, the hand held device acquires an image of the patient. Accordingly, the above mentioned model of the patient may be superimposed on the image acquired by the hand held device. It is noted that the systems described above in conjunction with FIGS. 9, 10, 11, 12, 13 and 14 are brought herein as examples only. The configuration of the detectors and light emitters may change according to specific needs. For example, all the optical detectors may be WFOV optical detectors. Alternatively, in FIGS. 10, 11 and 12 a WFOV optical detector may be located on the head of the physician and optical detectors on the patient and medical tool. In FIG. 9, the locations of the WFOV optical detector and the optical detector may be interchanged. Furthermore, in conjunction with FIGS. 9, 10, 11 and 12 the WFOV optical detector may be fitted with two light emitters and the optical detector with one light emitter. Additionally, more than three light emitters may be associated with each pair of reference location and target object, thus increasing the accuracy and reliability of the tracking system.

It will be appreciated by persons skilled in the art that the disclosed technique is not limited to what has been particularly shown and described hereinabove. Rather the scope of the disclosed technique is defined only by the claims, which follow.

The invention claimed is:

1. A medical Wide Field Of View optical tracking system for determining the position and orientation of a target object in a reference coordinate system comprising:
   at least three light emitters;
   at least one optical detector, at least one of said at least one optical detector being a Wide Field Of View optical detector, said Wide Field Of View optical detector acquiring at least one image of at least one light emitter within the field of view of said Wide Field Of View optical detector, each of said at least one Wide Field Of View optical detector including:
      an optical sensor, for sensing light received from said at least one light emitter within the field of view of said Wide Field Of View optical detector; and
      at least two optical receptors, optically coupled with said optical sensor, each of said optical receptors including an entrance pupil, said optical receptors being spatially spaced apart from each other, each of said optical receptors projecting a different angular section of an observed scene on said optical sensor;

a processor, coupled with each of said at least one optical detector, said processor determining the position and orientation of said target object in said reference coordinate system, at least according to representations of said at least three light emitters, wherein, each of said at least three light emitters is within the field of view of at least one of said at least one optical detector, wherein each one of said at least one optical detector and each one of said at least three light emitters is adapted to be attached to a respective one of said target object and a reference location, said reference location being associated with said reference coordinate system, and wherein said target object and said reference location are respective elements in a tuple including two elements from a group consisting of a display, a patient body location, a medical tool, physician body location, and a fixed position.

2. The medical Wide Field Of View optical tracking system according to claim 1 including at least two optical detectors, at least one of said at least two optical detectors is said Wide Field Of View optical detector, wherein each of said at least one Wide Field Of View optical detector and the at least one other optical detector are adapted to be attached to a respective different one of said target object and said reference location.

3. The medical Wide Field Of View optical tracking system according to claim 2, wherein each of said at least two detectors is a Wide Field Of View optical detector.

4. The medical Wide Field Of View optical tracking system according to claim 2, wherein said at least three light emitters are arranged in one of the configurations which at least include:

at least two light emitters attached to said target object and at least one light emitter attached to said reference location; and at least two light emitters attached to said reference location and at least one light emitter attached to said target object.

5. The medical Wide Field Of View optical tracking system according to claim 1 further including said display for displaying one of a real-time image, a model of a region of interest of a patient, navigational information, a representation of a medical tool.

6. The medical Wide Field Of View optical tracking system according to claim 5, wherein said at least one of said real-time image, said model of a region of interest of a patient, said navigational information, said representation of a medical tool, is registered with one of the respective coordinate system of at least another one of said real-time image, said model of a region of interest of a patient, said navigational information, said representation of a medical tool and said reference coordinate system.

7. The medical Wide Field Of View optical tracking system according to claim 5, further including a database for storing said model, said navigational information and said representation of a medical tool.

8. The medical Wide Field Of View optical tracking system according to claim 5, wherein said display is a head mounted display donned by a physician.

9. The medical Wide Field Of View optical tracking system according to claim 8 wherein said tuple includes at least said head mounted display and a patient and said processor determines at least the relative orientation between said head mounted display and said patient, wherein said processor renders the displayed ones of said model said navigational information said representation of a medical tool and said real-time image at an orientation corresponding to said relative orientation between said head mounted display and said patient, and wherein said head mounted display displays the rendered model to said physician.

10. The medical Wide Field Of View optical tracking system according to claim 8, wherein said tuple includes at least said head mounted display and a medical tool and said processor determines at least the relative orientation between said head mounted display and said medical tool, wherein said processor constructs a visual representation of said medical tool, and wherein said head up display further displays said visual representation of said medical tool to said physician.

11. The medical Wide Field Of View optical tracking system according claim 8, wherein the angle between the optical axis of said head mounted display and the optical detector attached to said head mounted display is fixed, and wherein said processor adjusts said orientation of the displayed ones of said model said navigational information said representation of a medical tool and said real-time image to account for said angle.

12. The medical Wide Field Of View optical tracking system according to claim 5, wherein said display is a hand held display.

13. The medical Wide Field Of View optical tracking system according to claim 5, wherein said tuple includes at least a medical tool, said medical tool being a real-time imager, said real-time imager acquires said real-time image.

14. The medical Wide Field Of View optical tracking system according to claim 13, wherein said real-time imager being one of:

an ultrasound imager;
a laparoscopic camera;
a X-ray imager located on a C-arm; and
a real-time MRI imager.

15. The medical Wide Field Of View optical tracking system according to claim 1, wherein at least one of said at least three light emitters is a light emitting diode.

16. The medical Wide Field Of View optical tracking system according to claim 1, wherein at least one of said at least three light emitters is a light reflector.

17. The medical Wide Field Of View optical tracking system according to claim 1, wherein said processor further associates each representation with a respective one optical receptor projecting the light received from said at least one light emitter on said optical sensor.

18. The medical Wide Field Of View optical tracking system according claim 17, wherein said position and orientation processor associates said at least one representation with a respective one optical receptor by tracking said representations.

19. The medical Wide Field Of View optical tracking system according to claim 17, wherein said position and orientation processor associates said at least one representation with a respective one optical receptor by determining a figure of merit for each association between said at least one representation and each optical receptor and selecting the association with the higher figure of merit.

20. The medical Wide Field Of View optical tracking system according to claim 17, wherein said position and orientation processor associates each one of said representations with a corresponding optical receptor, according to the geometric configuration of said at least two optical receptors.

21. The medical Wide Field Of View optical tracking system according to claim 1 wherein only at least one predefined region of interest within said at least one image is processed by at least one of said at least one optical detector and said processor,
  wherein the borders of said region of interest are determined according to the predicted location of a representation of said at least one light emitter in said at one image.

22. The medical Wide Field Of View optical tracking system according to claim 21, wherein said predicted location of said representation of said at least one light emitter in said at one image is determined based on the estimated relative orientation between the target object and the reference location as determined by a low accuracy tracker.

23. The medical Wide Field Of View optical tracking system according to claim 21, wherein said predicted location of said representation of said at least one light emitter in said at one image is determined according to the location of said representation of said light emitters in a previous at least one image and an estimation of motion of said target object.

24. The medical WFOV optical tracking system according to claim 1, wherein said a processor is wirelessly coupled with at least one of said at least one optical detector.

25. A medical Wide Field Of View optical tracking system for determining the position and orientation of a target object in a reference coordinate system comprising:
  at least one light emitter attached to said target object;
  at least one other light emitter attached to a reference location, said reference location being associated with said reference coordinate system;
  a Wide Field Of View optical detector acquiring at least one image of at least one light emitter within the field of view of said Wide Field Of View optical detector, said Wide Field Of View optical detector including:
    an optical sensor, for sensing light received from at least one of said at least one light emitter attached to said reference location; and
    at least two optical receptors, optically coupled with said optical sensor, each of said optical receptors including an entrance pupil, said optical receptors being spatially spaced apart from each other, each of said optical receptors projecting a different angular section of an observed scene on said optical sensor;
  another optical detector acquiring at least one image of at least one light emitters within the field of view of said at least one other optical detector; and
  a position and orientation processor, coupled with each of said at least one Wide Field of View optical detector, with each of said at least one other optical detector, said processor determining the position and orientation of each of said target object in said reference coordinate system, according to representations of said at least one light emitter attached said target object and at least one other light emitter attached to said reference location,
  wherein said target object and said reference location are one of respective elements in a tuple including two elements from a group consisting of a display, a patient body location, physician body location, and a medical tool,
  wherein each of said WFOV optical detector and said another optical detector is attached to a respective one of said elements,
  wherein one of said elements is designated as a reference location and the remaining one of said elements is designated as a target object, and
  wherein the total number of said light emitters is at least three.

* * * * *